(12) United States Patent
Ono et al.

(10) Patent No.: US 12,178,607 B2
(45) Date of Patent: Dec. 31, 2024

(54) BLOOD PRESSURE MEASUREMENT DEVICE

(71) Applicants: OMRON HEALTHCARE CO., LTD., Muko (JP); OMRON CORPORATION, Kyoto (JP)

(72) Inventors: Takashi Ono, Kyoto (JP); Takanori Nishioka, Kyoto (JP); Shinji Mizuno, Yasu (JP); Hirokazu Tanaka, Otsu (JP); Tomoyuki Nishida, Takatsuki (JP); Noboru Kohara, Okayama (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 765 days.

(21) Appl. No.: 17/358,458

(22) Filed: Jun. 25, 2021

(65) Prior Publication Data
US 2021/0315523 A1   Oct. 14, 2021

Related U.S. Application Data

(63) Continuation of application No. PCT/JP2019/048033, filed on Dec. 9, 2019.

(30) Foreign Application Priority Data

Dec. 27, 2018 (JP) .................. 2018-246152

(51) Int. Cl.
*A61B 5/00* (2006.01)
*A61B 5/0235* (2006.01)

(52) U.S. Cl.
CPC ............ *A61B 5/681* (2013.01); *A61B 5/0235* (2013.01)

(58) Field of Classification Search
CPC ....... A61B 5/02; A61B 5/021; A61B 5/02141; A61B 5/022; A61B 5/0235; A61B 5/681; A61B 5/6831; A61B 2560/04
See application file for complete search history.

(56) References Cited

U.S. PATENT DOCUMENTS

2016/0041531 A1* 2/2016 Mackie .................. A61B 5/681
368/80
2017/0215749 A1* 8/2017 Zhuo .................. A61B 5/02055
(Continued)

FOREIGN PATENT DOCUMENTS

JP   2010-017602 A   1/2010
JP   2016-104224 A   6/2016
(Continued)

OTHER PUBLICATIONS

Feb. 10, 2020 Search Report issued in International Patent Application No. PCT/JP2019/048033.
(Continued)

*Primary Examiner* — Eric F Winakur
*Assistant Examiner* — Abel Seifu Abegaz
(74) *Attorney, Agent, or Firm* — Oliff PLC

(57) ABSTRACT

A blood pressure measurement device includes: a case including; a strap; a plurality of valves; a pump; and a power supply unit. The pump and the power supply unit are disposed with a gap therebetween. The pump is provided with a suction hole on a surface thereof opposite to the power supply unit. The device comprises a hole portion formed between each of a pairs of lugs of an outer case, an opening end being located at a position opposed to the gap in a first direction. The hole portion extends linearly, and one opening end of the hold portion is provided on the outer surface of the outer case closer to a wrist, and other opening (Continued)

end thereof is provided on the inner surface of the outer case closer to a windshield than the one opening end.

5 Claims, 30 Drawing Sheets

(56) References Cited

U.S. PATENT DOCUMENTS

2018/0092550 A1  4/2018  Sprenger et al.
2018/0140209 A1  5/2018  Ono et al.

FOREIGN PATENT DOCUMENTS

| JP | 6172351 B1 * | 8/2017 | ............. A61B 5/022 |
| JP | 2018-000692 A | 1/2018 | |
| JP | 2018-143557 A | 9/2018 | |

OTHER PUBLICATIONS

Jul. 1, 2021 International Preliminary Report on Patentability issued in International Patent Application No. PCT/JP2019/048033.

\* cited by examiner

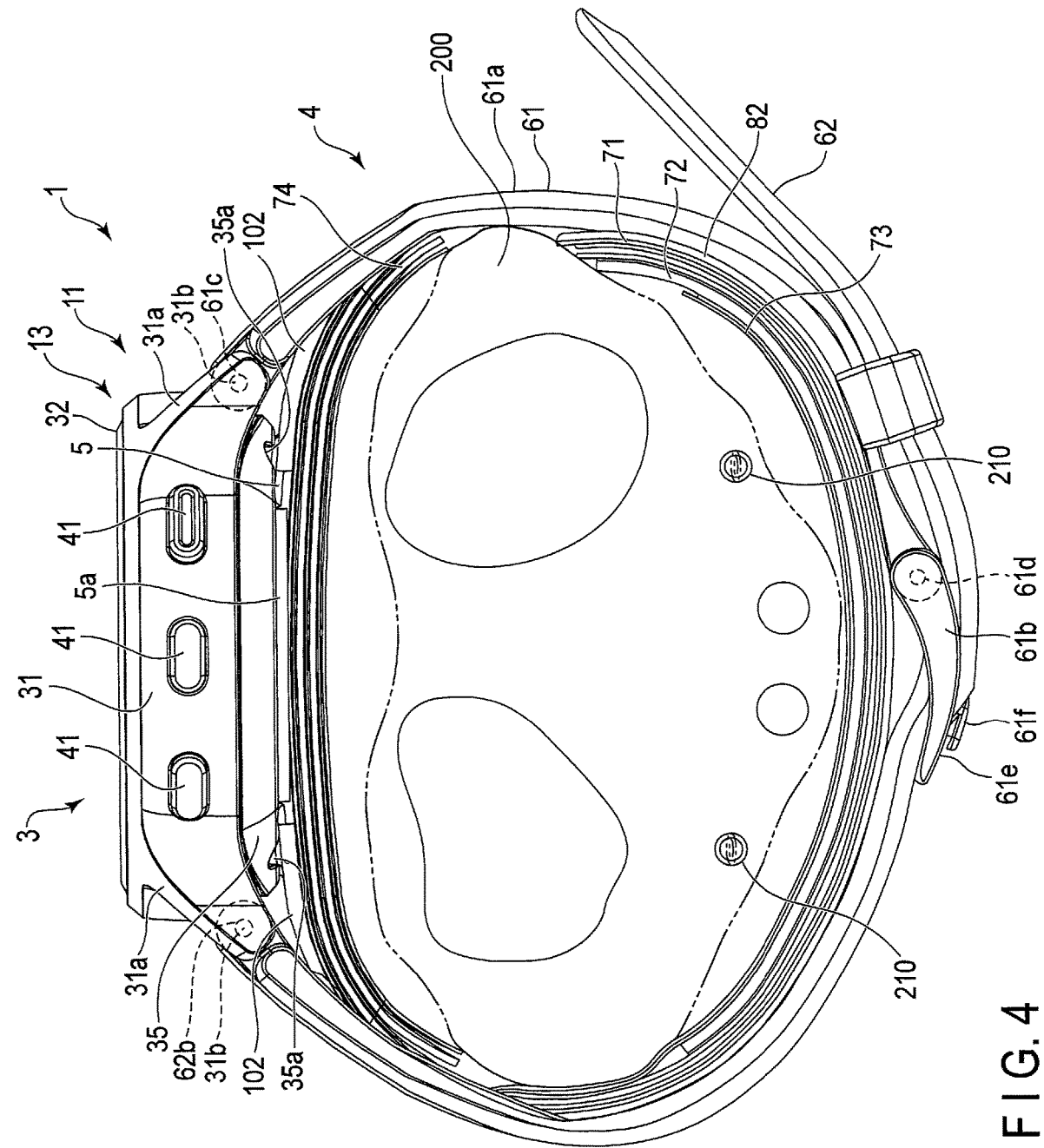
F I G. 4

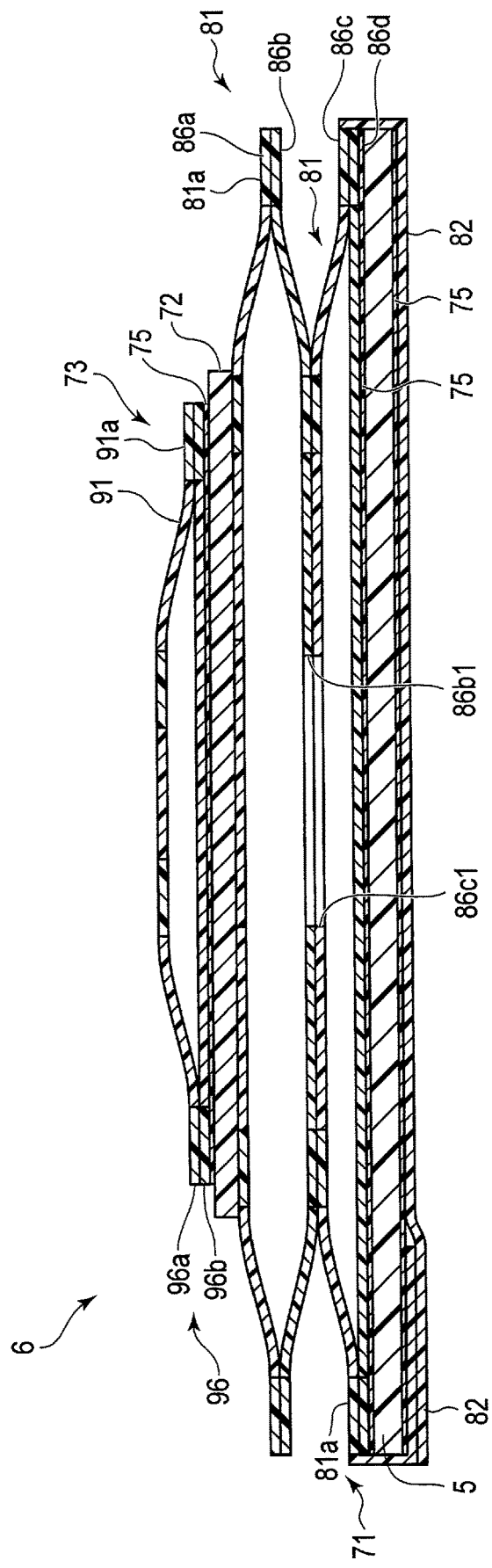
F I G. 16

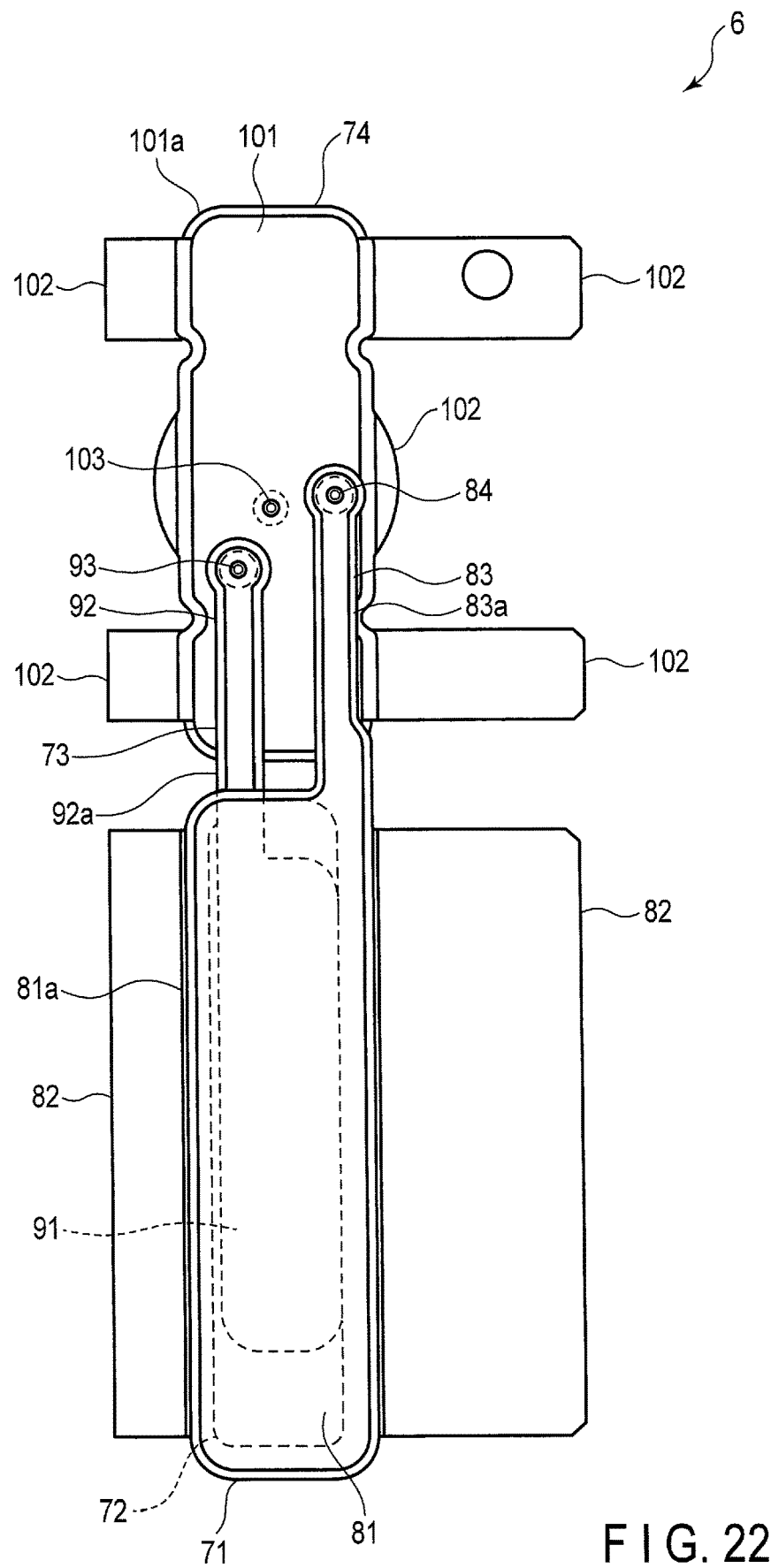
F I G. 22

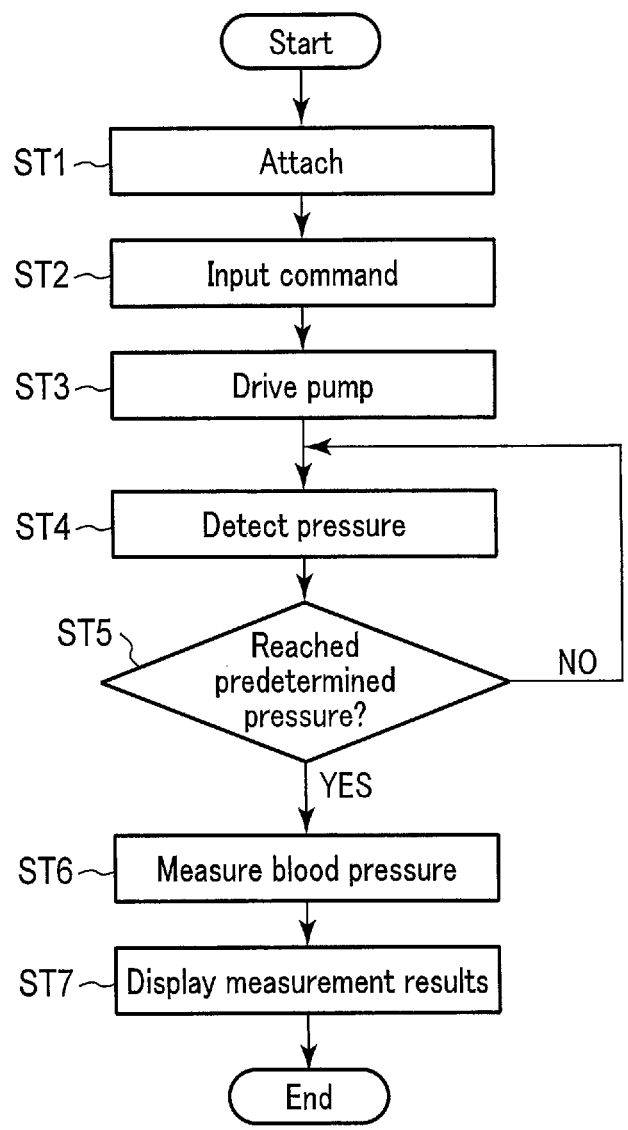
F I G. 27

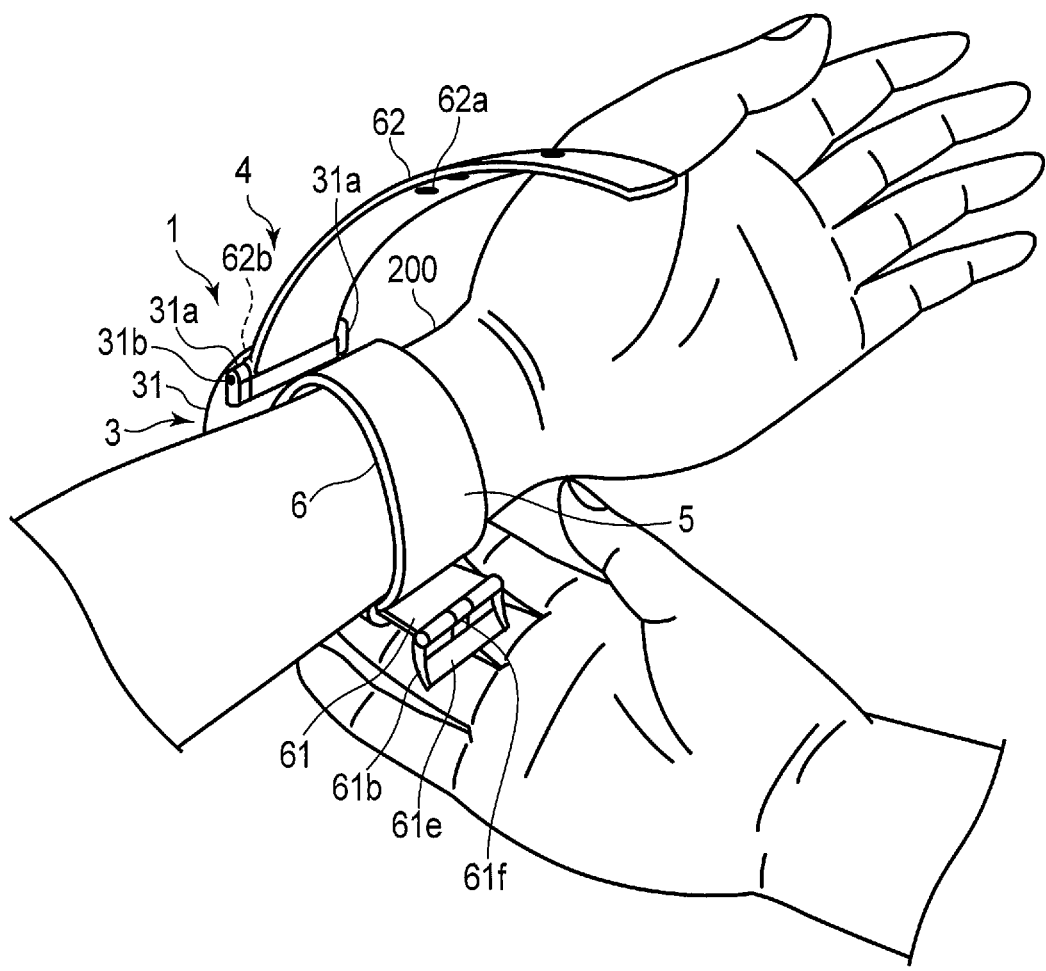
F I G. 28

BLOOD PRESSURE MEASUREMENT DEVICE

CROSS-REFERENCE TO RELATED APPLICATIONS

This is a Continuation Application of PCT application No. PCT/JP2019/048033, filed Dec. 9, 2019, which was published under PCT Article 21(2) in Japanese.

This application is based upon and claims the benefit of priority from Japanese Patent Application No. 2018-246152, filed Dec. 27, 2018, the entire contents of which are incorporated herein by reference.

FIELD

The present invention relates to a blood pressure measurement device that measures blood pressure.

BACKGROUND

In recent years, blood pressure measurement devices used for measuring blood pressure are used not only in medical facilities but also at home as a means for confirming a health condition. A blood pressure measurement device measures blood pressure by detecting the vibration of the arterial wall, for example, by inflating and contracting a cuff wrapped around the upper arm, wrist or the like of a living body and detecting the pressure of the cuff with a pressure sensor.

As a blood pressure measurement device as described above, there is known what is called an integral blood pressure measurement device in which a cuff and a device body for supplying fluid to the cuff are formed integrally with each other. In addition, the integral blood pressure measurement device could be a wearable device that is worn on the wrist.

The device body of the blood pressure measurement device includes a case, a pump cased in the case and supplying fluid to the cuff, and a battery cased in the case and applying power to the pump. It is known that the pump and the battery are spaced apart from each other in a direction orthogonal to the axial direction of the case as disclosed in, for example, Jpn. Pat. Appln. KOKAI Publication No. 2018-000692 (see, for example, patent literature 1).

CITATION LIST

Patent Literature

Patent literature 1: Jpn. Pat. Appln. KOKAI Publication No. 2018-000692

The foregoing blood pressure measurement device may be configured to include a plurality of cuffs. In a configuration including a plurality of cuffs, a valve is provided in a flow path connected to a pump and the cuffs. The valve is opened and closed to selectively open and close the flow path connected from the pump to each of the cuffs. In a configuration in which a valve is placed in a case, the case is increased in size because a space is secured for placing the valve in the case. If the valve is particularly placed in alignment with the battery or pump of the case in the axial direction, the case is thickened in the axial direction.

It is therefore an object of the present invention to provide a blood pressure measurement device capable of thinning a case.

SUMMARY

According to one aspect, there is provided a blood pressure measurement device attached to a wrist, including: a case including an outer case formed in a cylindrical shape and having a pair of lugs provided at each of positions symmetrical in a circumferential direction of an outer surface, and a windshield covering one end of the outer case; a strap including a first strap provided on one pair of lugs through a spring rod and a second strap provided on other pair of lugs through a spring rod; a plurality of valves provided in a flow path that supplies a fluid to a cuff inflated by the fluid in the outer case in a position which is closer to one side of the outer case than a center thereof in a second direction orthogonal to a first direction from the one pair of lugs to the other pair of lugs and orthogonal to an axial direction of the outer case; a pump provided in the outer case closer to the center of the outer case with respect to the valves in the second direction and on one side from the center of the outer case in the first direction; and a power supply unit cased in the outer case, disposed in the pump alongside the windshield in the axial direction of the outer case and opposed to the pump.

It should be noted here that the fluid includes liquid and air. When blood pressure is measured, the cuff is wrapped around, for example, the upper arm or wrist of a living body, and is inflated with a fluid supplied to the cuff. The cuff includes a bag-shaped structure such as an air bag.

According to this aspect, in the outer case, a region where the pump and the power supply unit are arranged and a region where the valves are arranged are separated from each other in a direction orthogonal to the axial direction of the outer case. Since, therefore, the valves do not overlap the pump or the power supply unit in the axial direction of the outer case, the blood pressure measurement device can be thinned in the axial direction of the outer case.

In the blood pressure measurement device according to the above aspect, there is provided a blood pressure measurement device wherein the pump and the power supply unit are disposed with a gap therebetween; the pump is provided with a suction hole on a surface thereof opposite to the power supply unit; and the device comprises a hole portion formed between each of the pairs of lugs of the outer case to pass through the outer case and having an opening end on an inner surface of the outer case, the opening end being located at a position opposed to the gap in the first direction.

According to this aspect, the gap between the pump and the power supply unit can prevent heat of the pump from being transferred to the power supply unit. Since, furthermore, the opening edge provided on the inner surface of the outer case is opposed to the gap between the pump and the power supply unit in the first direction, air flowing into the case through the opening edge is smoothly guided into the suction hole. Since, moreover, the air flowing into the case through the opening edge is applied to the surface of the pump, the pump can be cooled.

In the blood pressure measurement device according to the above aspect, there is provided a blood pressure measurement device including: a double-sided tape provided between opposing surfaces of the power supply unit and the pump to fixing the power supply unit and the pump at both edge portions of the pump in the second direction.

According to this aspect, the gap between the pump and the power supply unit can be provided using the thickness of the double-sided tape. Thus, no structure for providing gap between the pump and the power supply unit is required.

Since, furthermore, the double-side tape is provided at either edge of the pump in the second direction, it can prevent the inhibition of flow of air in the gap.

In the blood pressure measurement device according to the above aspect, there is provided a blood pressure measurement device wherein the power supply unit is formed in a long shape in one direction, a longitudinal direction of the power supply unit is along the first direction, and one side of the power supply unit in the longitudinal direction is opposed to face the pump.

According to this aspect, when the power supply unit is inflated by its deterioration and thus the center of the pump-side surface of the power supply unit is elevated toward the pump, a gap between one end of the pump and that of the power supply unit is increased on the hole portion opening edge side. The increase of this gap makes it possible to apply more air to the opposing surfaces of the pump and the power supply unit and accordingly the pump and the power supply unit can be improved in cooling efficiency, with the result that the power supply unit can be prevented from being deteriorated. In addition, the flow of more air into the gap can lower the resistance of an air flow path from outside the case to the suction hole of the pump through the hole portion.

In the blood pressure measurement device according to the above aspect, there is provided a blood pressure measurement device wherein the suction hole is formed at least on a surface of the pump opposed to the power supply unit on a hole portion side in the first direction and at either end of the pump in the second direction.

According to this aspect, even though the power supply unit is inflated by its deterioration and the center of the pump-side surface of the power supply unit is elevated toward the pump, the suction hole of the pump can be prevented from being blocked by the power supply unit.

In the blood pressure measurement device according to the above aspect, there is provided a blood pressure measurement device wherein the hole portion extends linearly, and one opening end of the hold portion is provided on the outer surface of the outer case closer to the wrist, and other opening end thereof is provided on the inner surface of the outer case closer to the windshield than the one opening end.

According to this aspect, the air flow path from outside the case to the suction hole of the pump through the hole portion can be prevented from being bent greatly. The resistance of the air flow path can thus be lowered.

In the blood pressure measurement device according to the above aspect, there is provided a blood pressure measurement device wherein the opening end of the hole portion formed between the one-paired lugs, which is provided on the outer surface of the outer case, is covered with the first strap; and the opening end of the hole portion formed between the other-paired lugs, which is provided on the outer surface of the outer case, is covered with the second strap.

According to this aspect, since the hole portion is covered with the strap, it can be prevented from being exposed outward.

Advantageous Effects

The present invention makes it possible to provide a blood pressure measurement device capable of thinning a case.

BRIEF DESCRIPTION OF THE DRAWINGS

FIG. 4 is an illustration of a state in which the blood pressure measurement device is worn on the wrist.

FIG. 16 is a sectional view showing a configuration of the curler and cuff structure of the blood pressure measurement device.

FIG. 22 is a plan view showing a configuration of the cuff structure.

FIG. 27 is a flowchart showing an example of the use of the blood pressure measurement device.

FIG. 28 is a perspective view showing an example of wearing the blood pressure measurement device on the wrist.

DETAILED DESCRIPTION

An example of a blood pressure measurement device 1 according to one embodiment of the present invention will be described below with reference to FIGS. 1 to 31.

Figure 1:
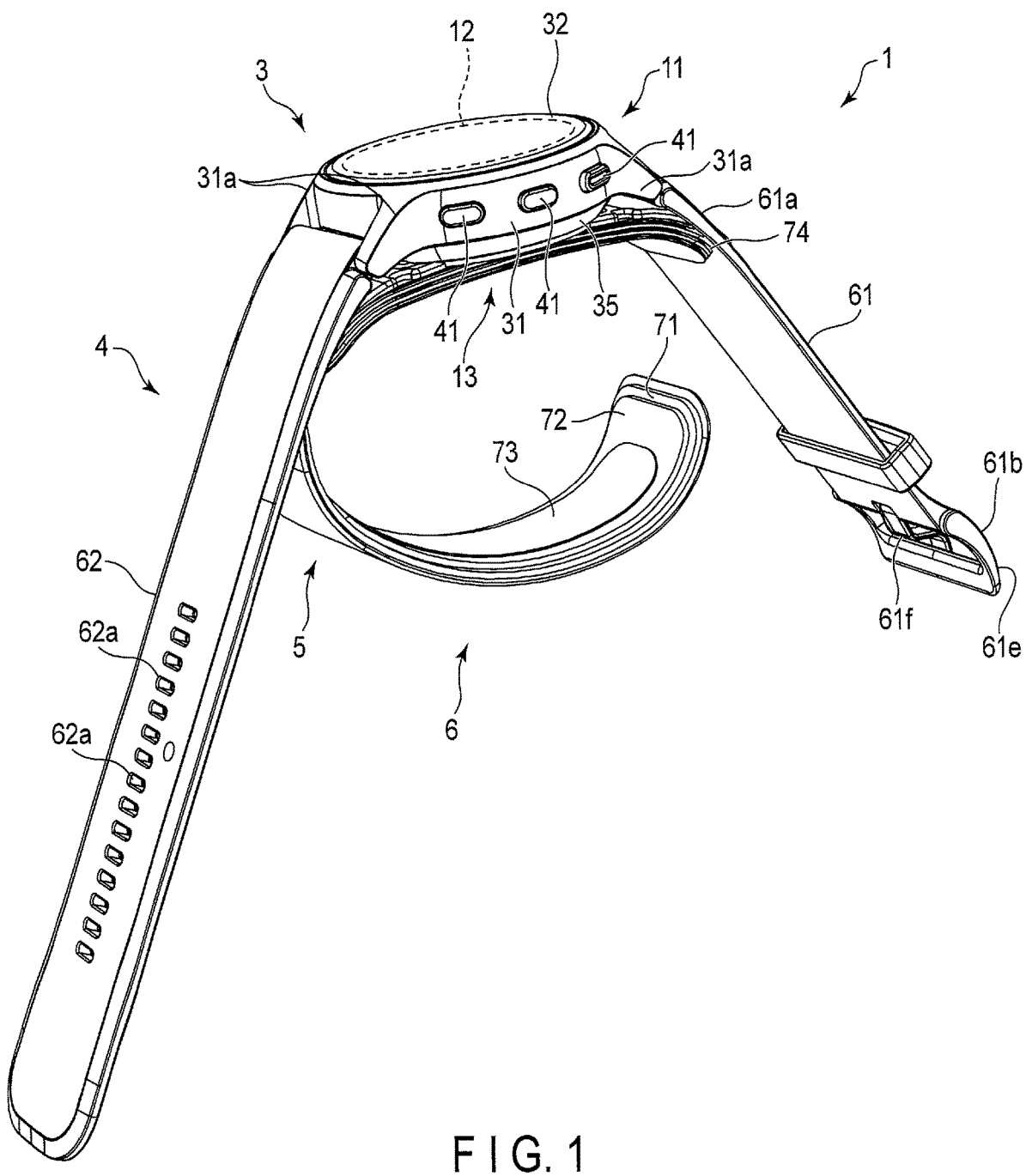
FIG. 1 is a perspective view showing a configuration of a blood pressure measurement device according to an embodiment of the present invention.
Figure 2:
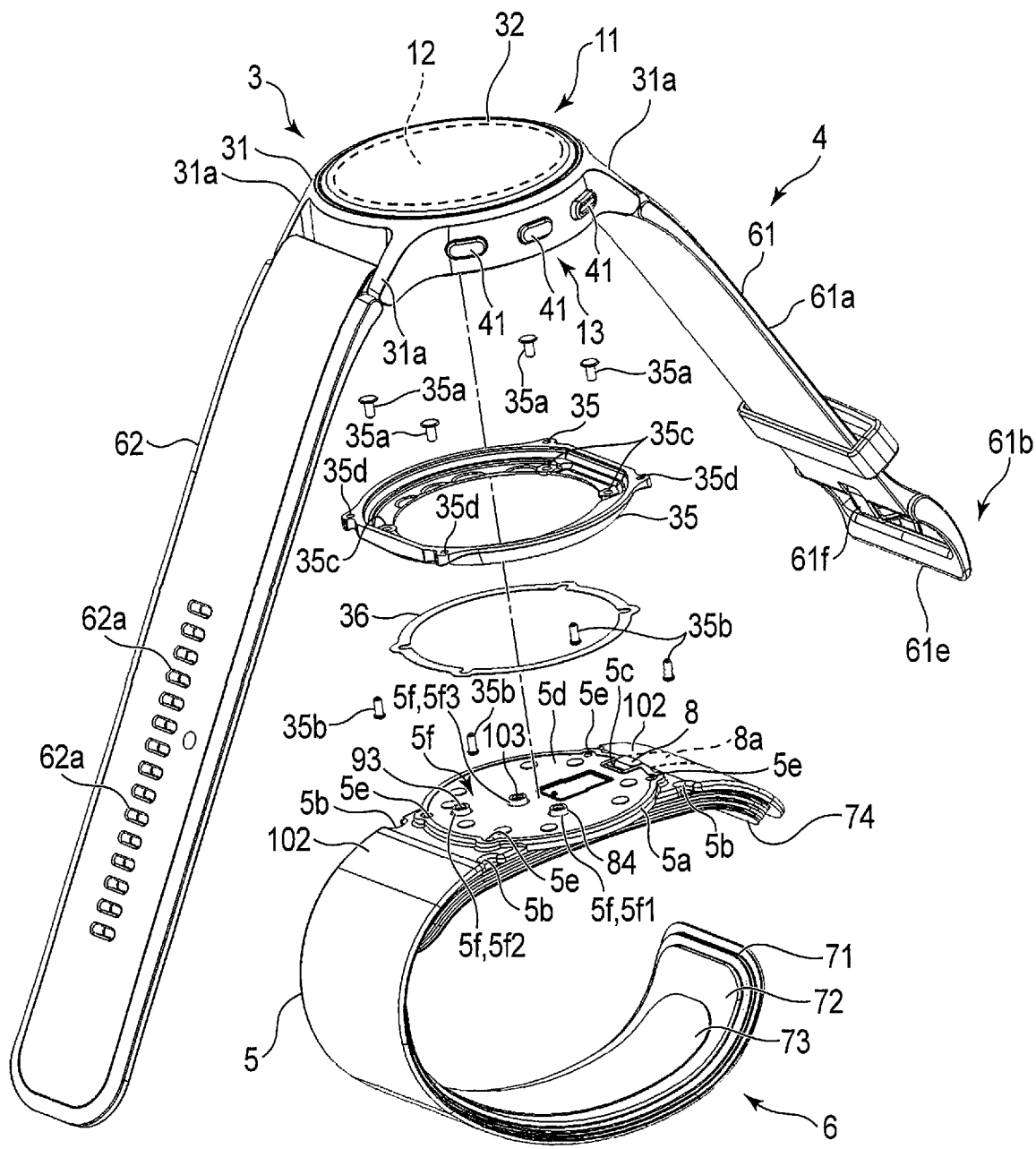
FIG. 2 is an exploded perspective view showing a configuration of the blood pressure measurement device.
Figure 3:
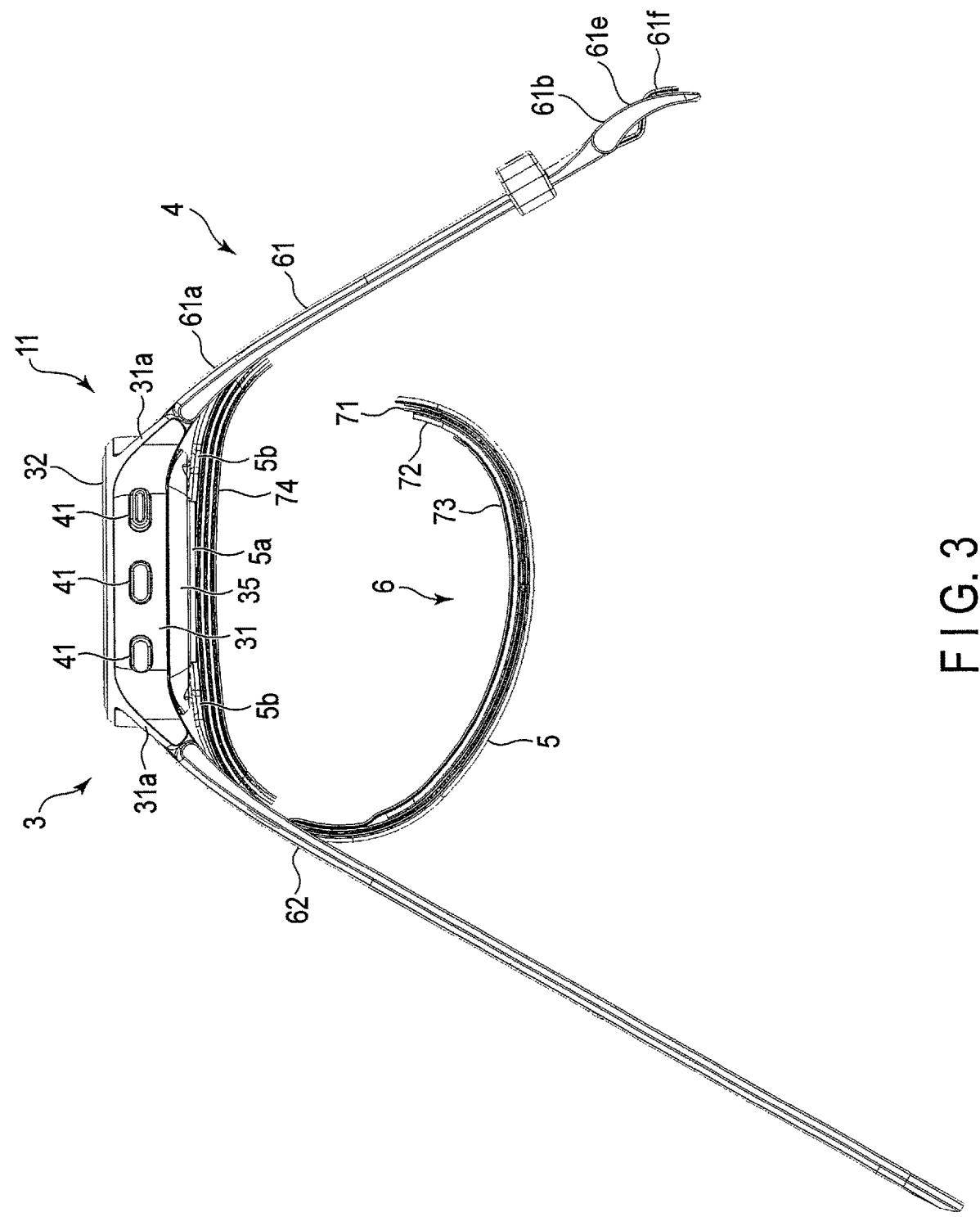
FIG. 3 is a side view showing a configuration of the blood pressure measurement device.
Figure 5:
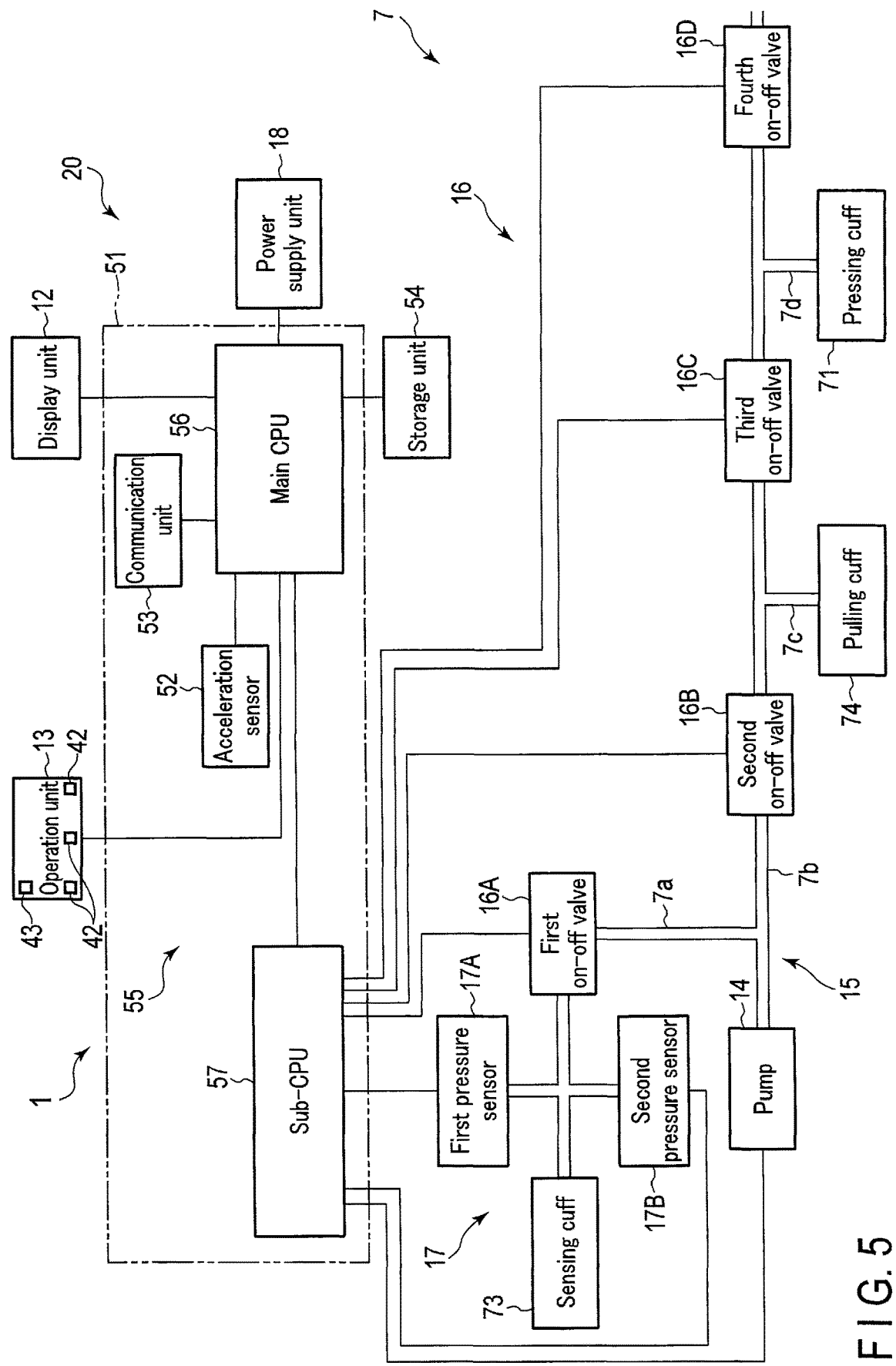
FIG. 5 is a block diagram showing a configuration of the blood pressure measurement device.
Figure 6:
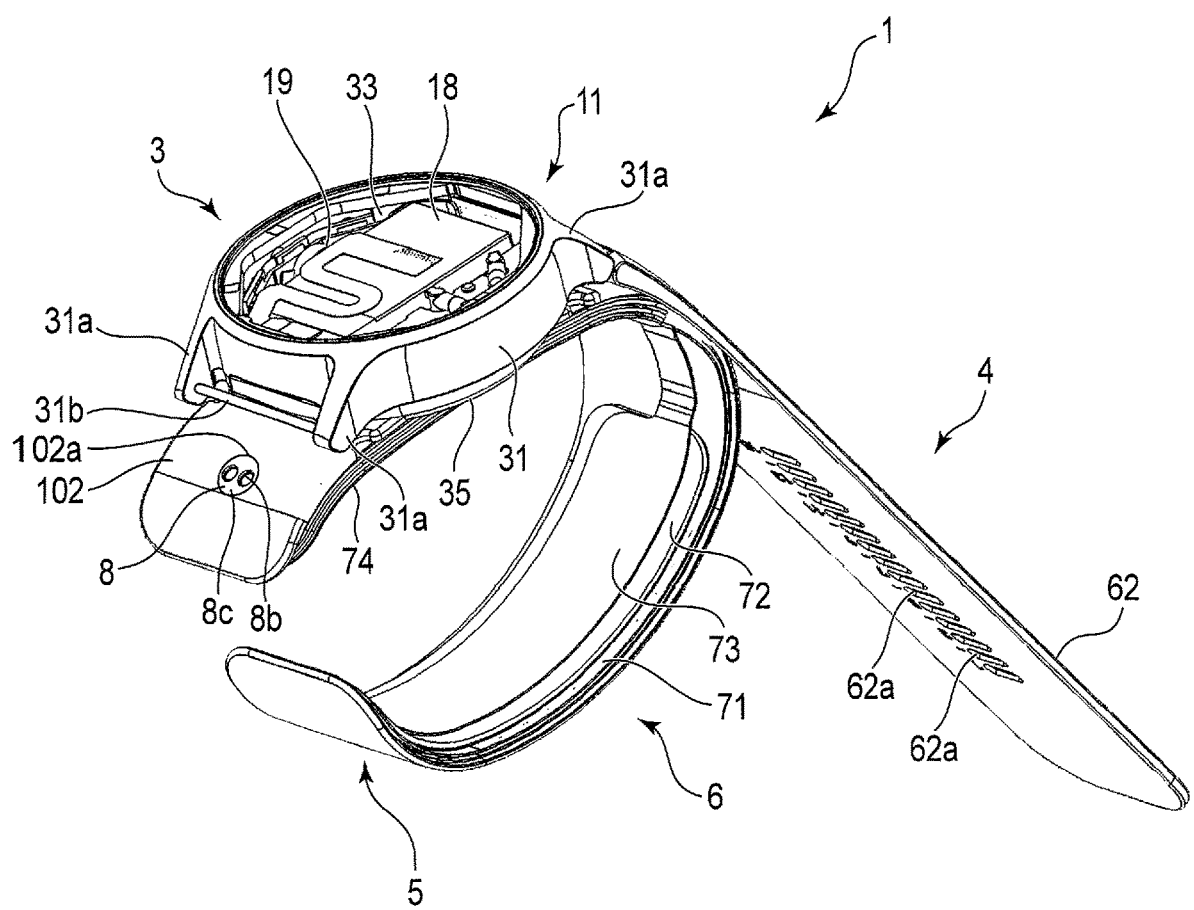
FIG. 6 is a perspective view showing a configuration of the blood pressure measurement device.
Figure 7:
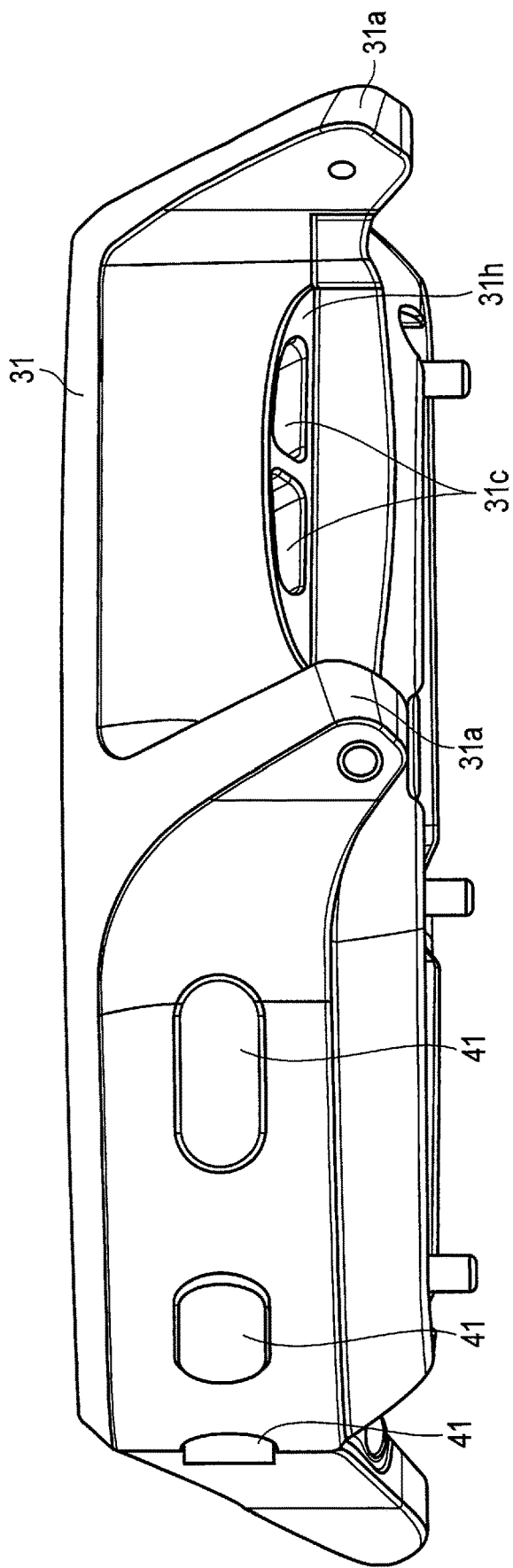
FIG. 7 is a perspective view showing a configuration of an outer case of the blood pressure measurement device.
Figure 8:
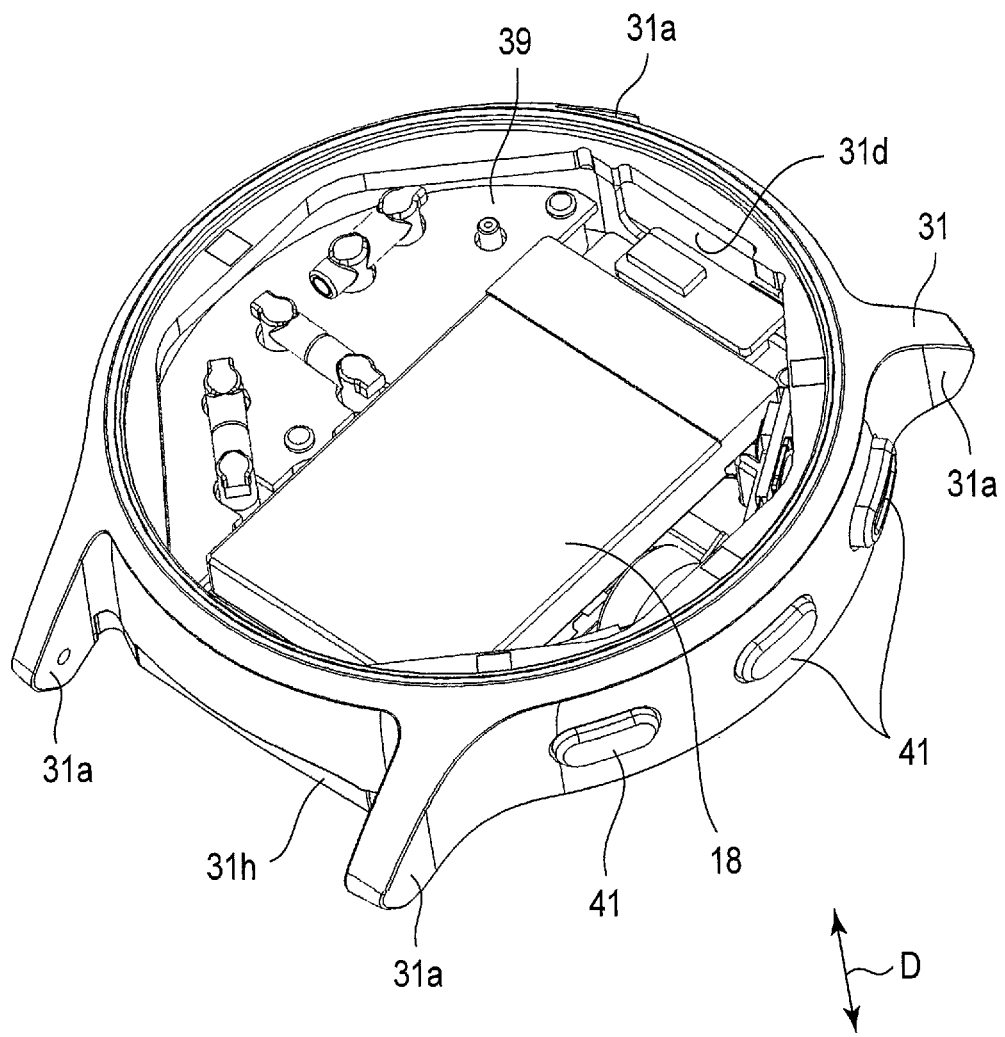
FIG. 8 is a perspective view showing a configuration of the blood pressure measurement device.
Figure 9:
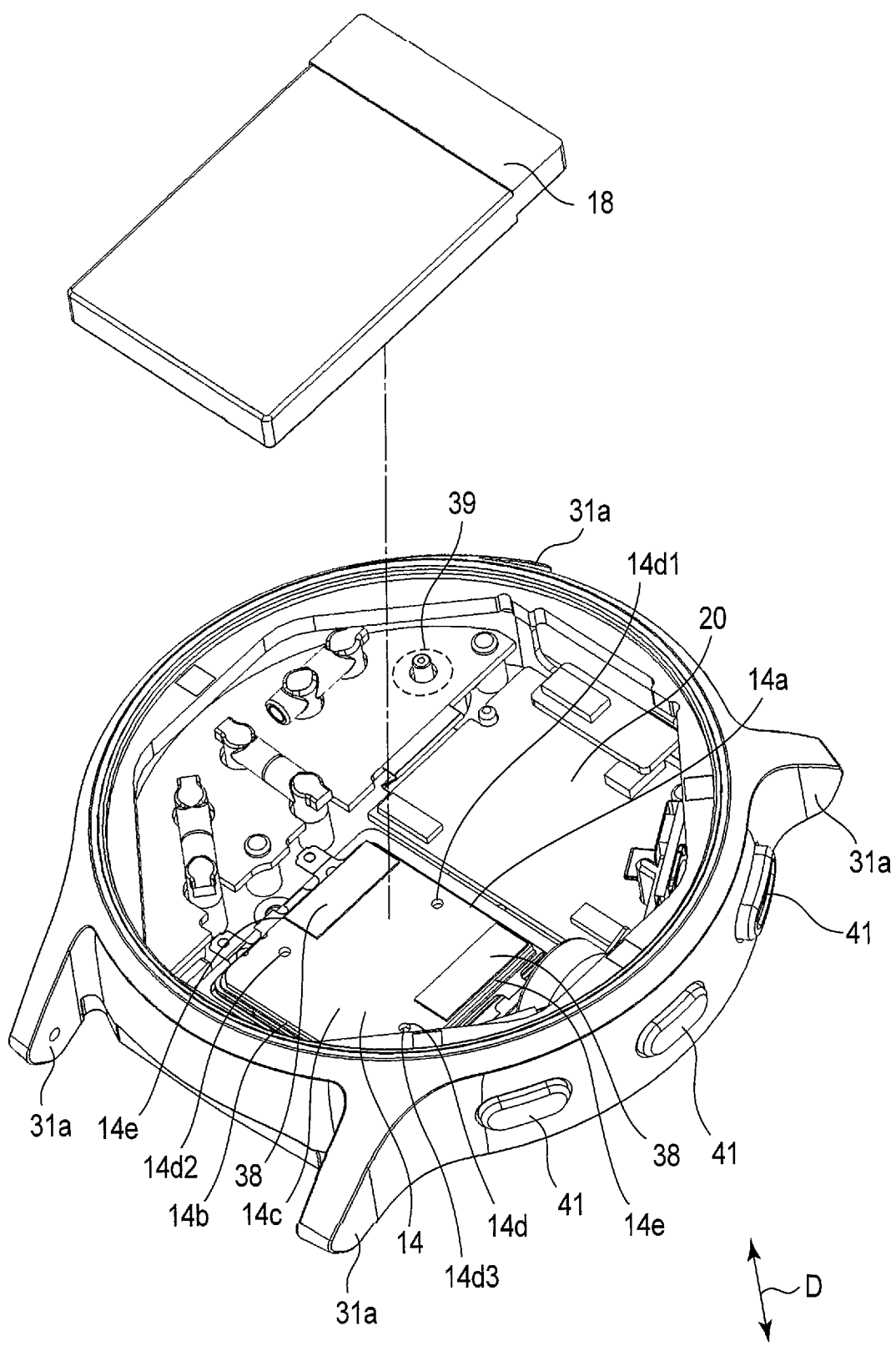
FIG. 9 is a partially exploded perspective view showing a configuration of the blood pressure measurement device.
Figure 10:
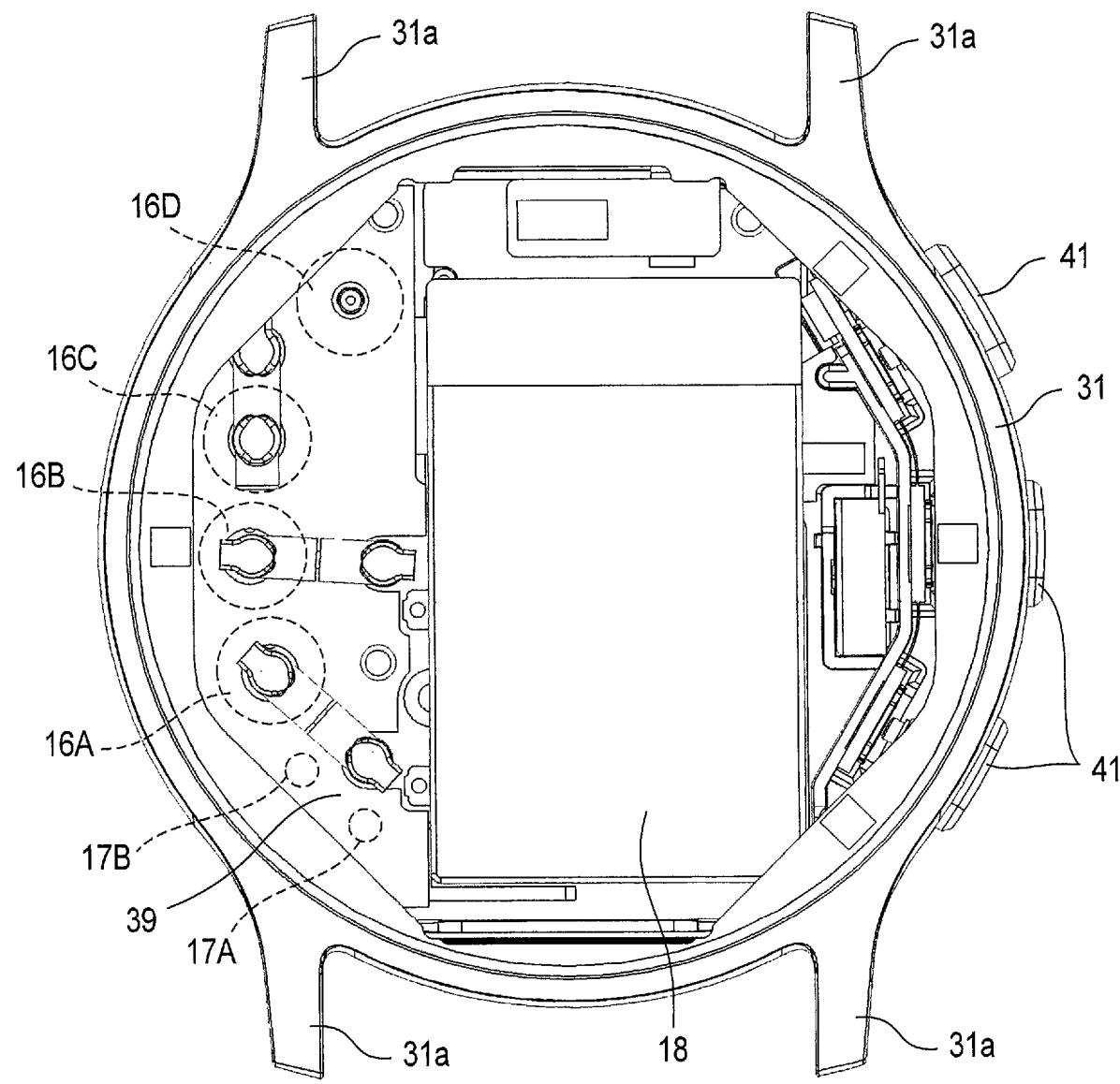
FIG. 10 is a plan view showing a configuration of the blood pressure measurement device.
Figure 11:
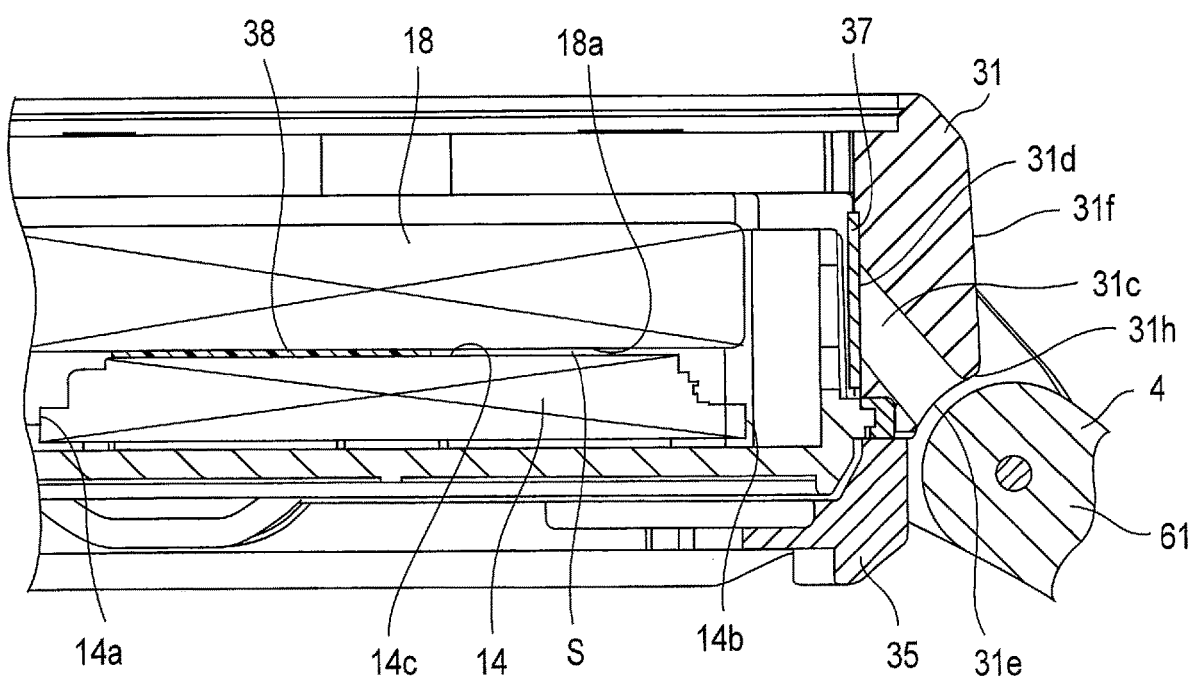
FIG. 11 is a sectional view showing a configuration of the outer case.

FIG. 1 is a perspective view showing a configuration of the blood pressure measurement device 1 according to the embodiment of the present invention. FIG. 2 is an exploded perspective view showing a configuration of the blood pressure measurement device 1. FIG. 3 is a side view showing a configuration of the blood pressure measurement device 1. FIG. 4 is an illustration of a state in which the blood pressure measurement device 1 is worn on the wrist 200. FIG. 5 is a block diagram showing a configuration of the blood pressure measurement device 1. FIG. 6 is a perspective view showing a configuration of the blood pressure measurement device 1. FIG. 7 is a perspective view showing a configuration of an outer case 31 of the blood pressure measurement device 1. FIG. 8 is a partially cutaway perspective view showing a configuration of the blood pressure measurement device 1 and specifically showing an interior configuration of a case 11 of the blood pressure measurement device 1. FIG. 9 is a partially exploded perspective view showing a configuration of the blood pressure measurement device 1 and specifically showing an exploded state of a power supply unit 18. FIG. 10 is a partially cutaway plan view showing a configuration of the blood pressure measurement device 1 and specifically showing a configuration of the case 11 of the blood pressure measurement device 1. FIG. 11 is a sectional view showing a configuration of a hole 31c of the outer case 31 and the vicinity thereof.

Figure 12:
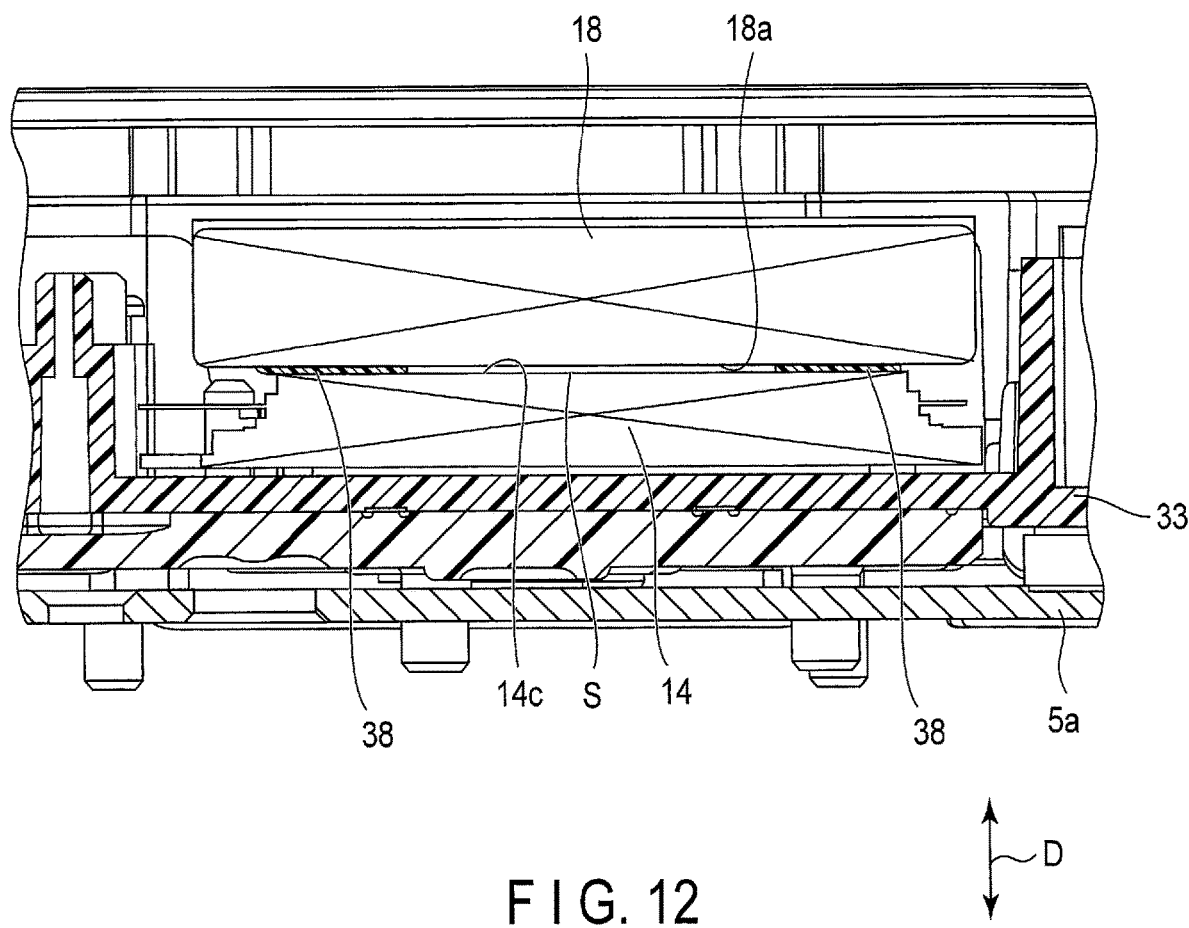
FIG. 12 is a sectional view showing a configuration of the blood pressure measurement device.
Figure 13:
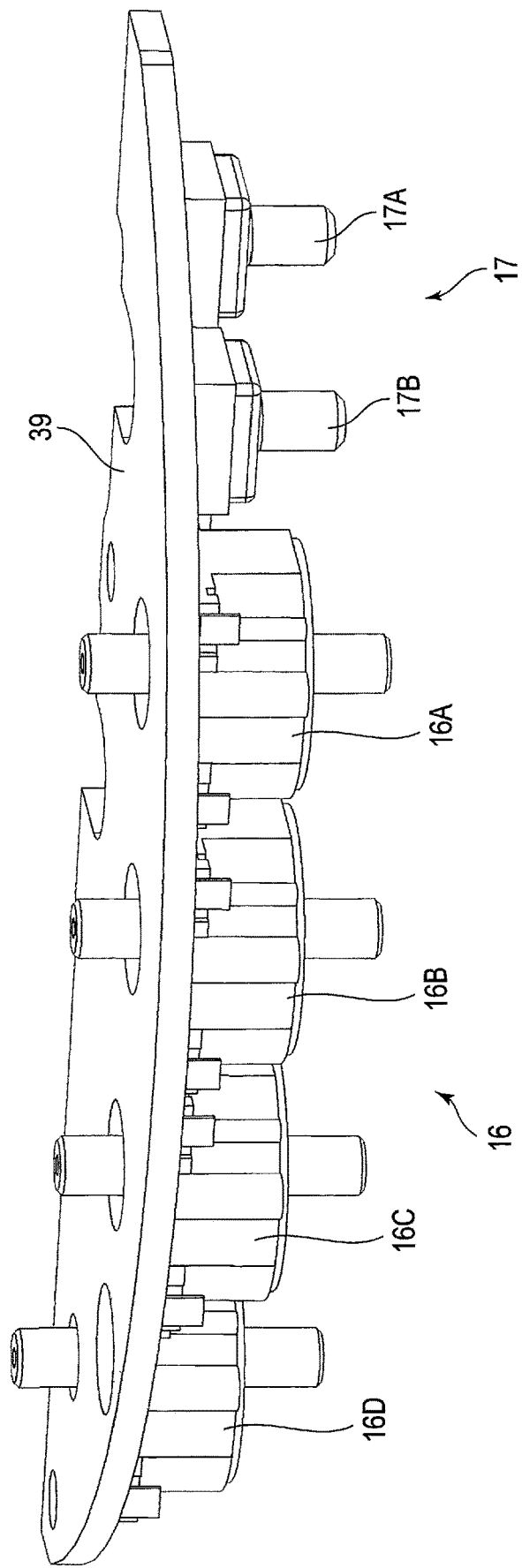
FIG. 13 is a perspective view showing a configuration of an on-off valve and a pressure sensor of the blood pressure measurement device.
Figure 14:
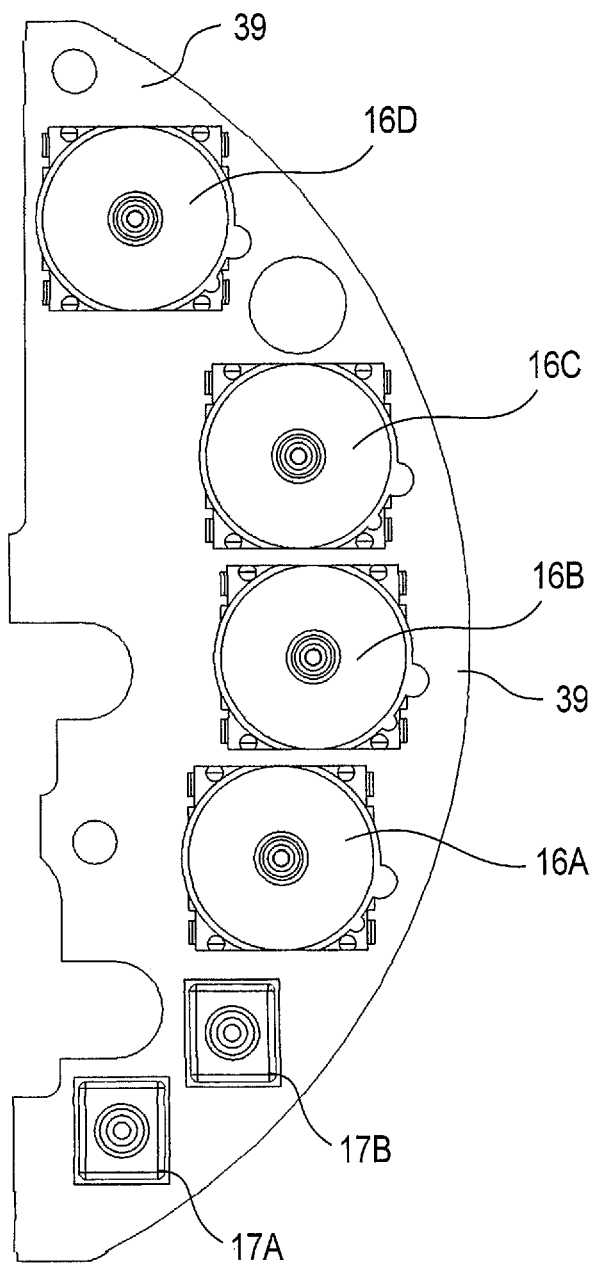
FIG. 14 is a plan view showing a configuration of the on-off valve and the pressure sensor of the blood pressure measurement device.

FIG. 12 is a sectional view showing a configuration of the blood pressure measurement device 1 and specifically showing a configuration of a pump 14 and power supply unit 14 and the vicinity thereof. FIG. 13 is a perspective view showing a configuration of an on-off valve 16 and a pressure sensor 17. FIG. 14 is a plan view showing a configuration of the on-off valve 16 and pressure sensor 17 when viewed from the wrist 200.

Figure 15:
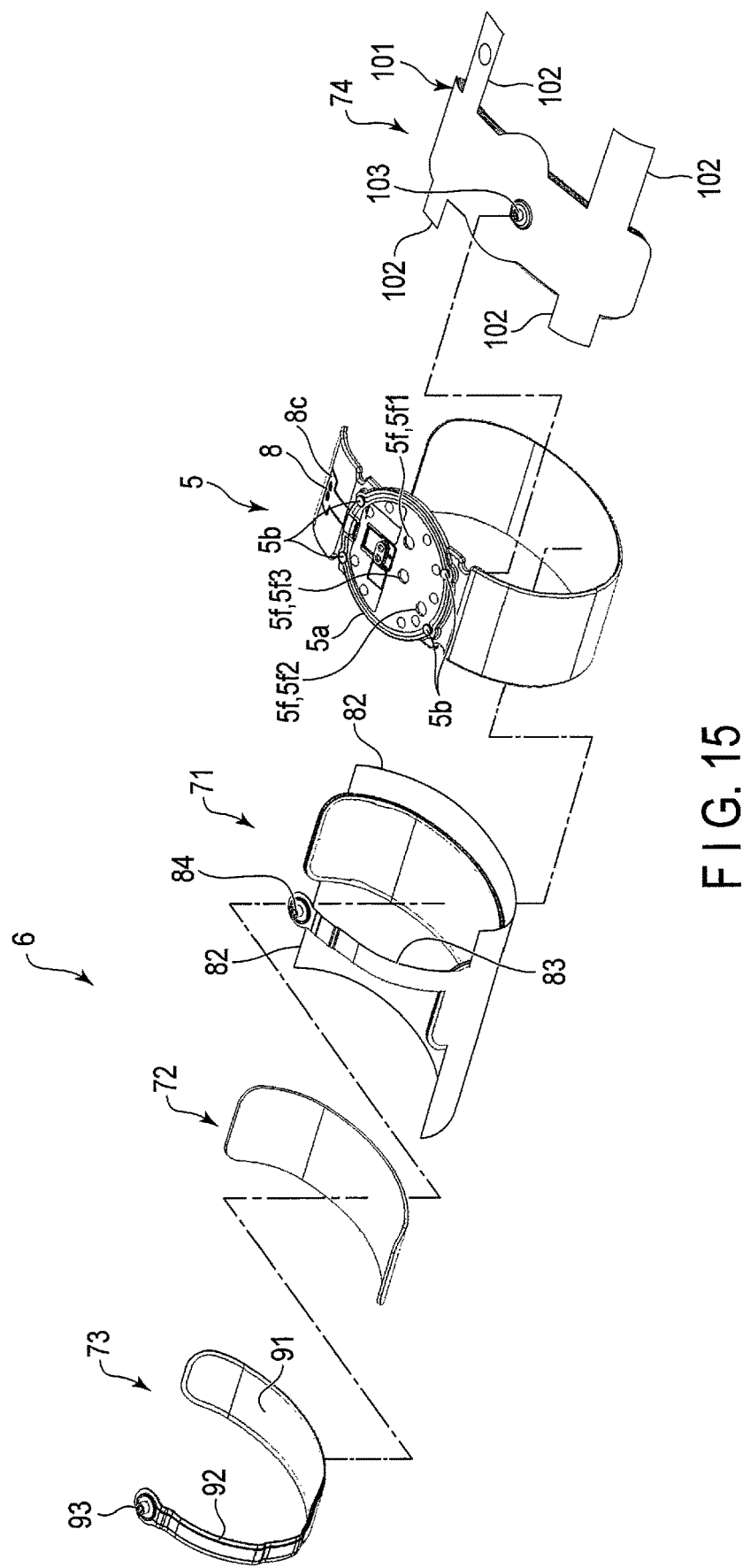
FIG. 15 is an exploded perspective view showing a configuration of a curler and a cuff structure of the blood pressure measurement device.
Figure 17:
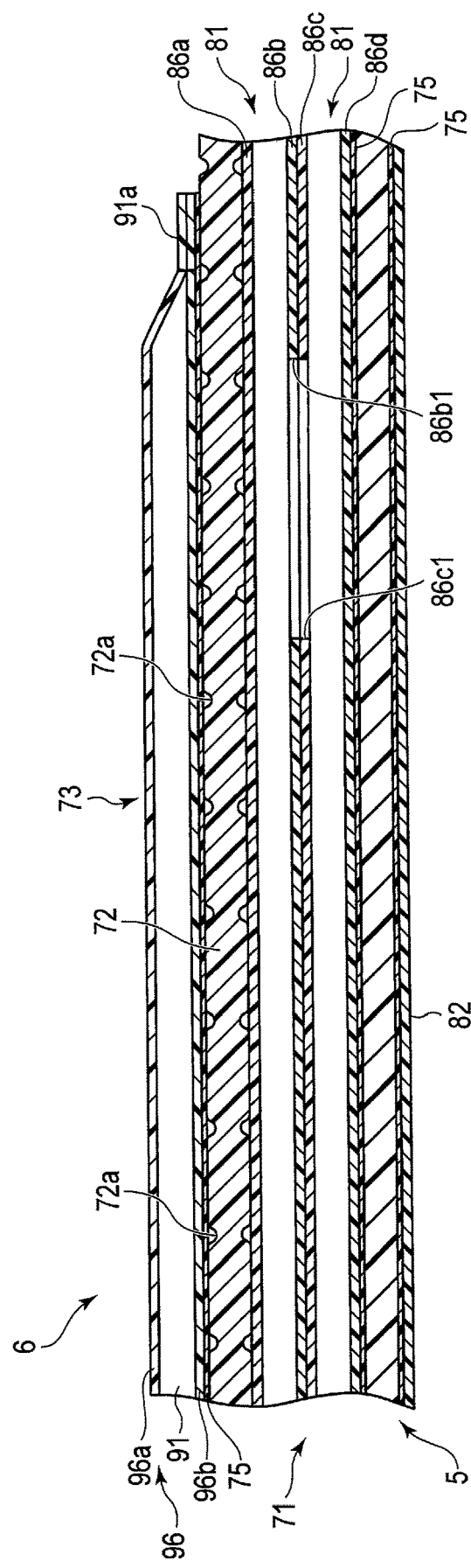
FIG. 17 is a sectional view showing a configuration of the curler and cuff structure of the blood pressure measurement device.

FIG. 15 is an exploded perspective view showing a configuration of a curler 5 and a cuff structure 6 of the blood pressure measurement device 1. FIG. 16 is a sectional view showing a configuration of the curler 5 and cuff structure 6 of the blood pressure measurement device 1. FIG. 17 is a sectional view showing a configuration of the curler 5 and cuff structure 6 of the blood pressure measurement device 1.

Figure 18:
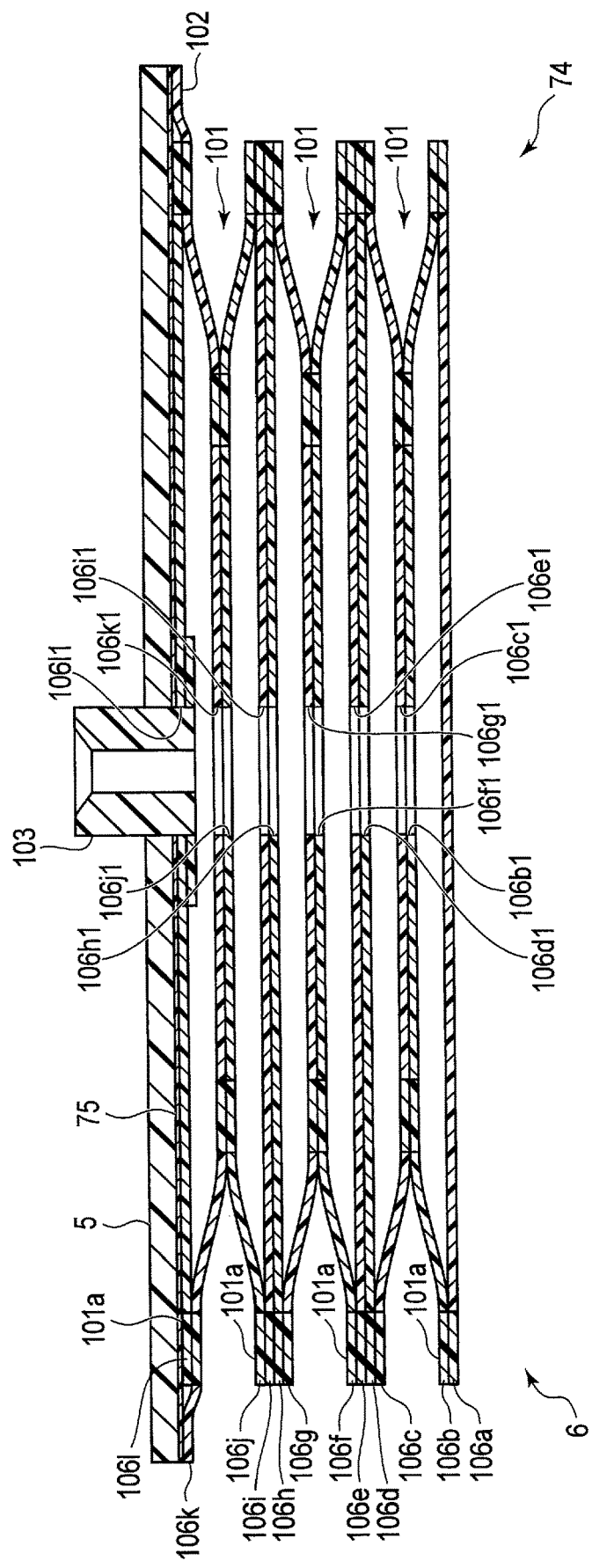
FIG. 18 is a sectional view showing a configuration of a back cuff of the blood pressure measurement device.
Figure 19:
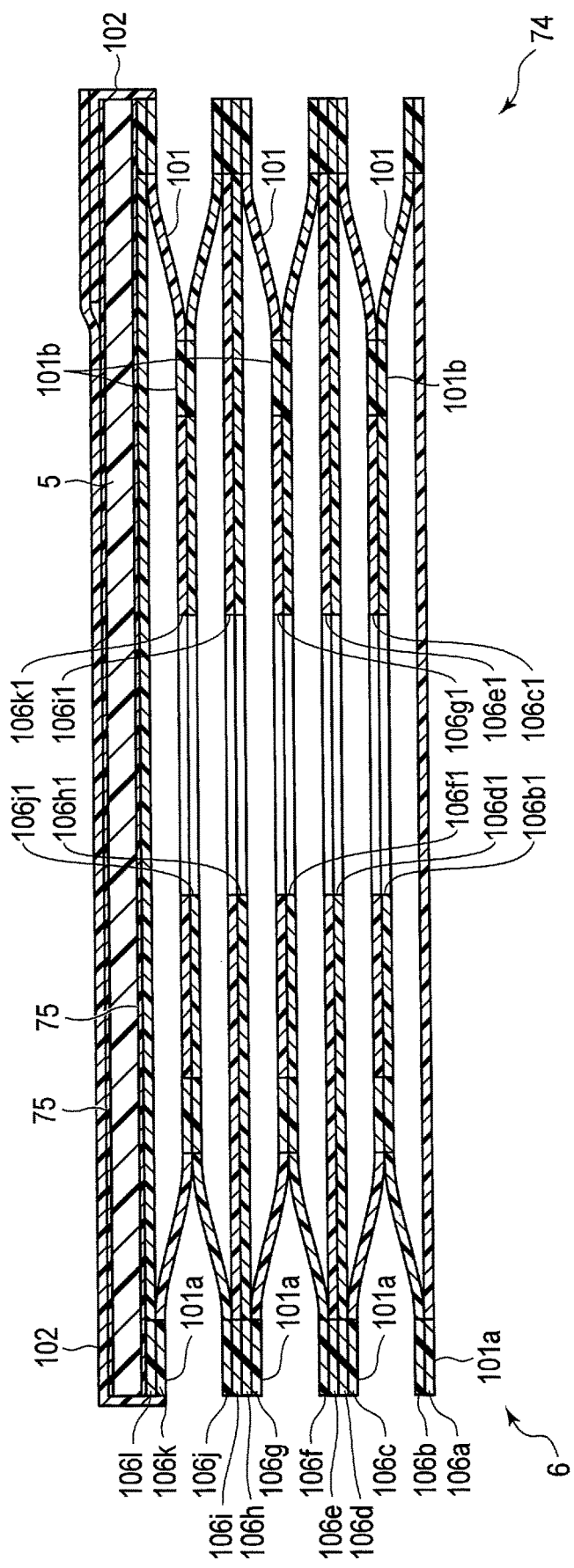
FIG. 19 is a sectional view showing a configuration of the back cuff of the blood pressure measurement device.
Figure 20:
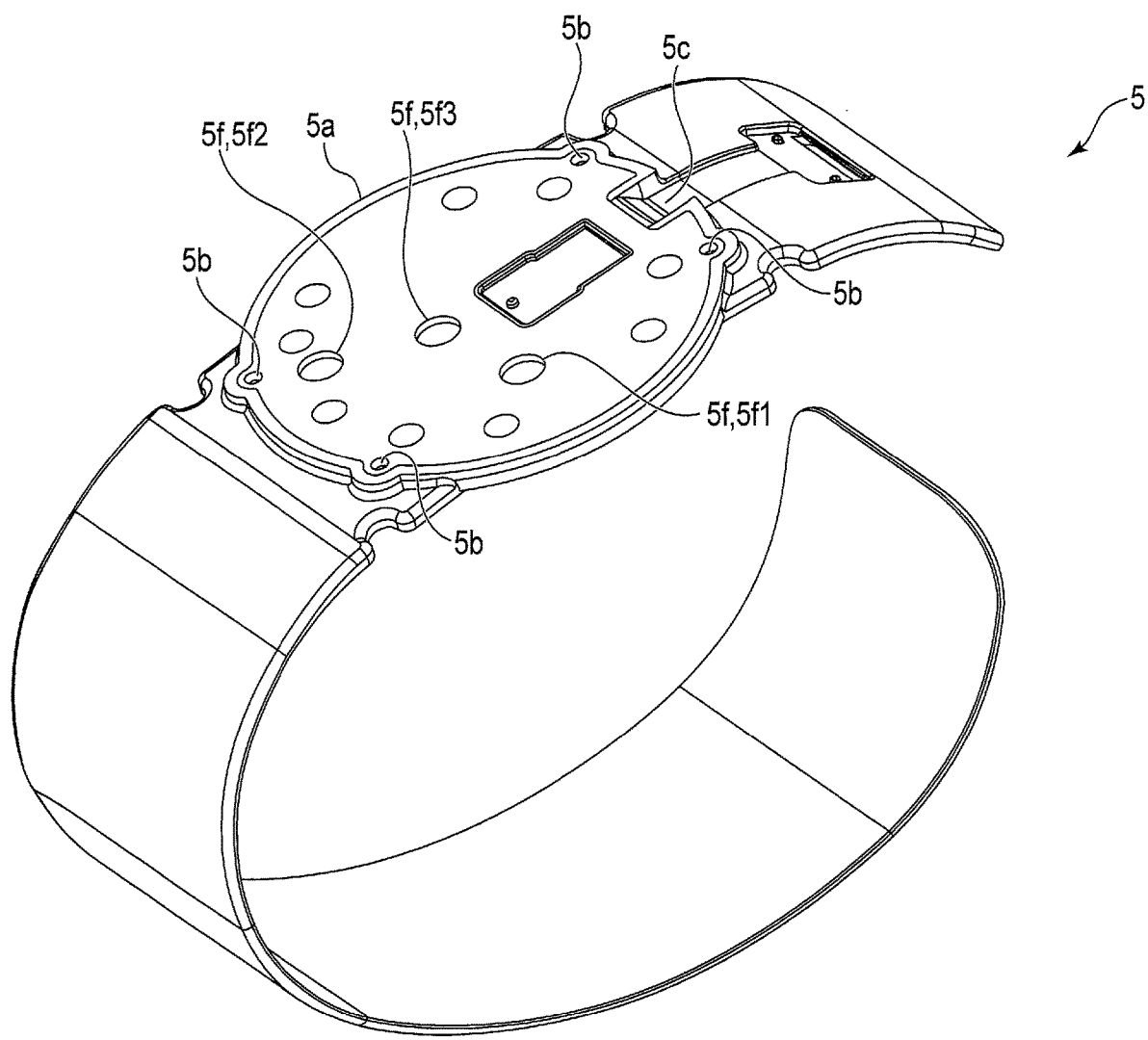
FIG. 20 is a perspective view showing a configuration of the curler of the blood pressure measurement device.
Figure 21:
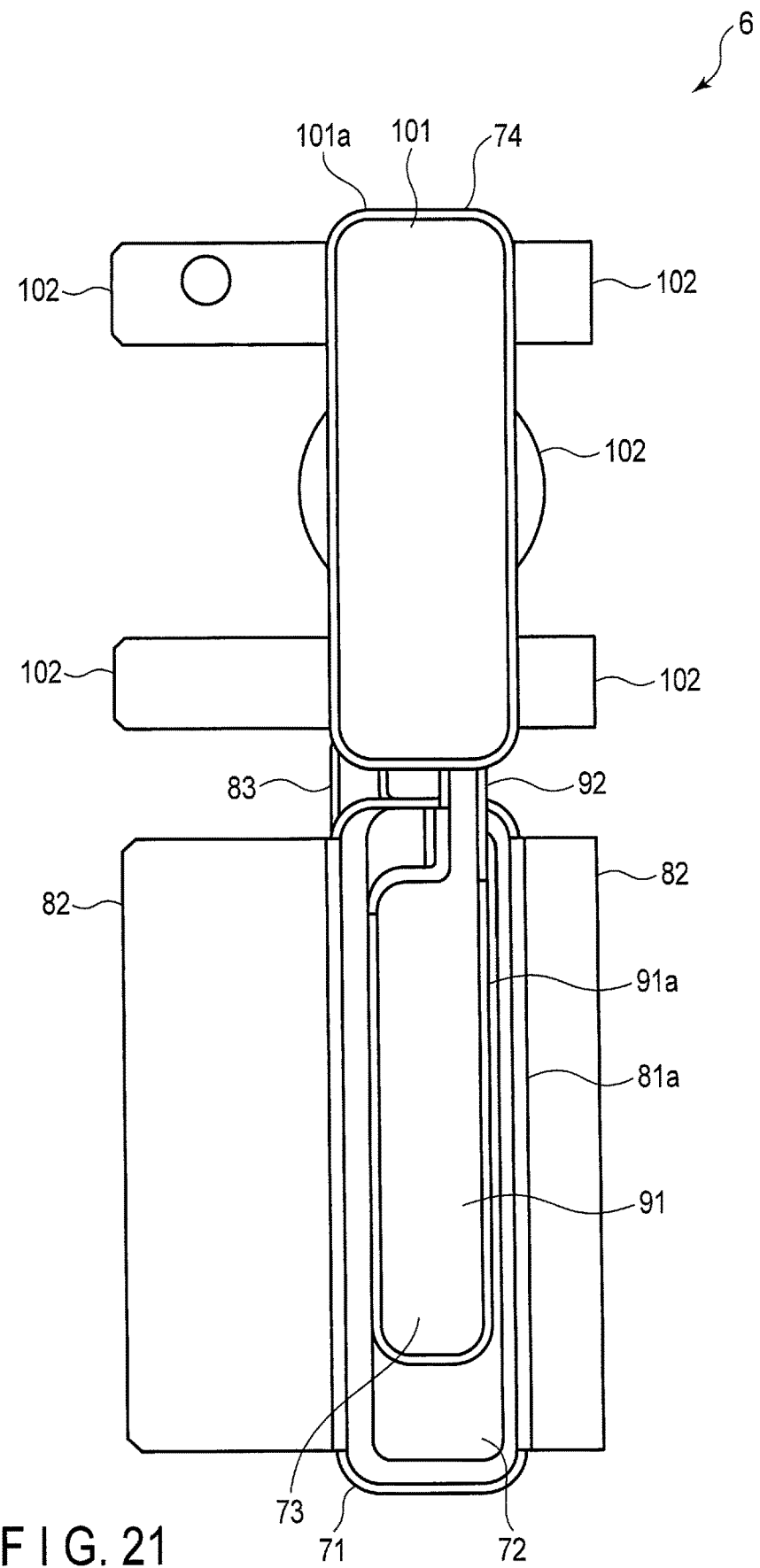
FIG. 21 is a plan view showing a configuration of the cuff structure of the blood pressure measurement device.
Figure 23:
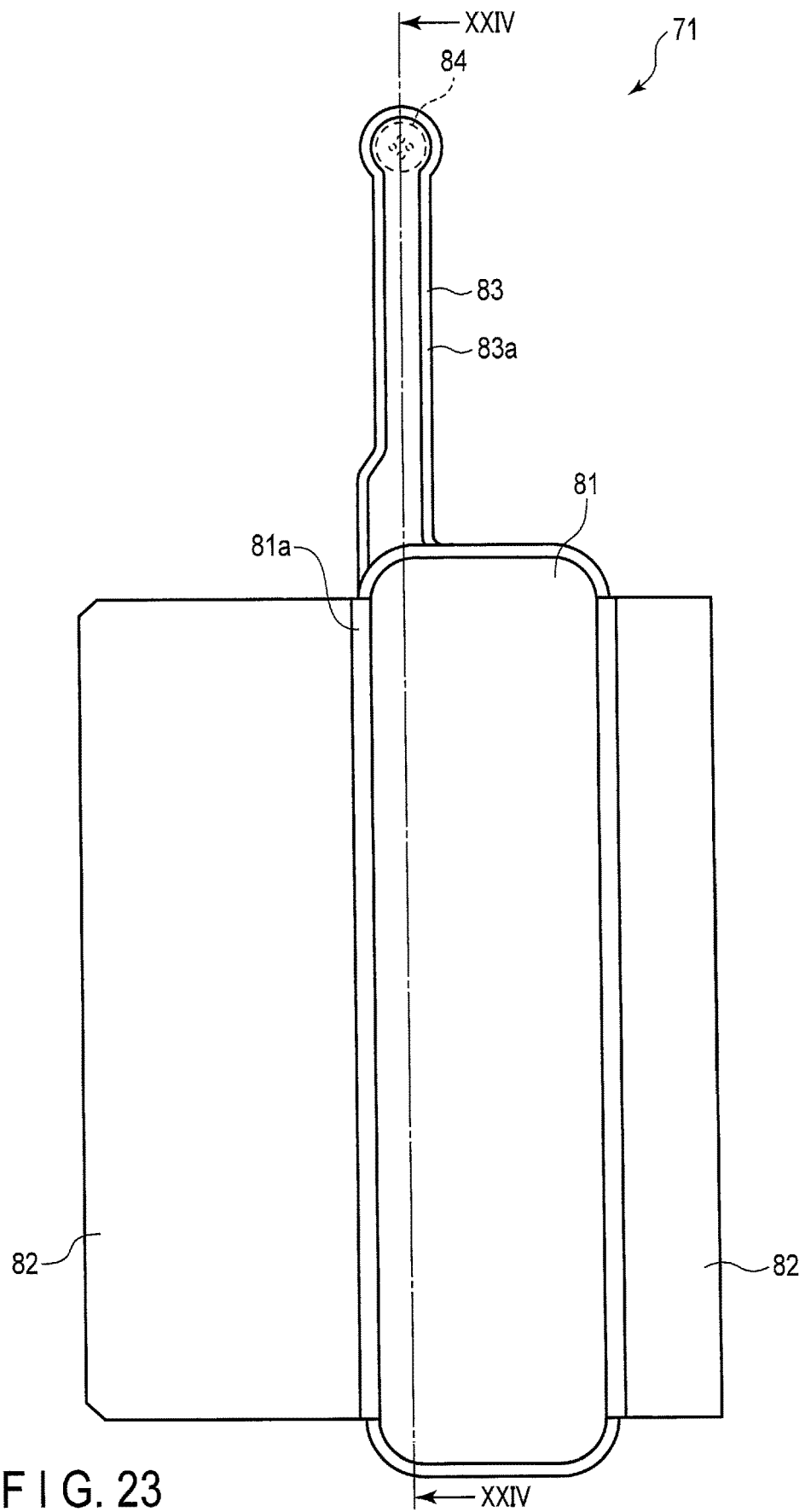
FIG. 23 is a plan view showing a configuration of a pressing cuff of the blood pressure measurement device.
Figure 24:
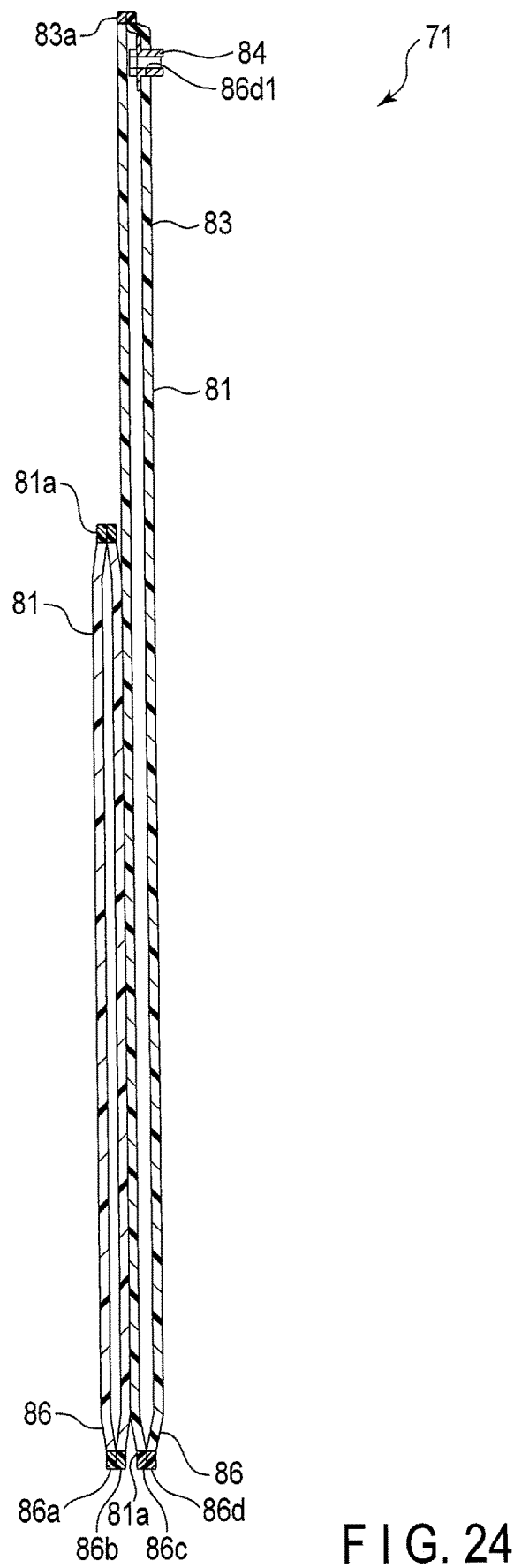
FIG. 24 is a sectional view showing a configuration of the pressing cuff.

FIG. 18 is a sectional view showing a configuration of a pulling cuff 74 of the blood pressure measurement device 1. FIG. 19 is a sectional view showing a configuration of the pulling cuff 74 of the blood pressure measurement device 1. FIG. 20 is a perspective view showing a configuration of the curler 5 of the blood pressure measurement device 1. FIG. 21 is a plan view showing a configuration of the cuff structure 6 of the blood pressure measurement device 1 when viewed from the wrist 200. FIG. 22 is a plan view showing a configuration of the cuff structure 6 when viewed from the inner surface of the curler 5. FIG. 23 is a plan view showing a configuration of a pressing cuff 71 of the blood pressure measurement device 1. FIG. 24 is a sectional view showing a configuration of the pressing cuff 71 along line XXIV-XXIV in FIG. 23.

Figure 25:
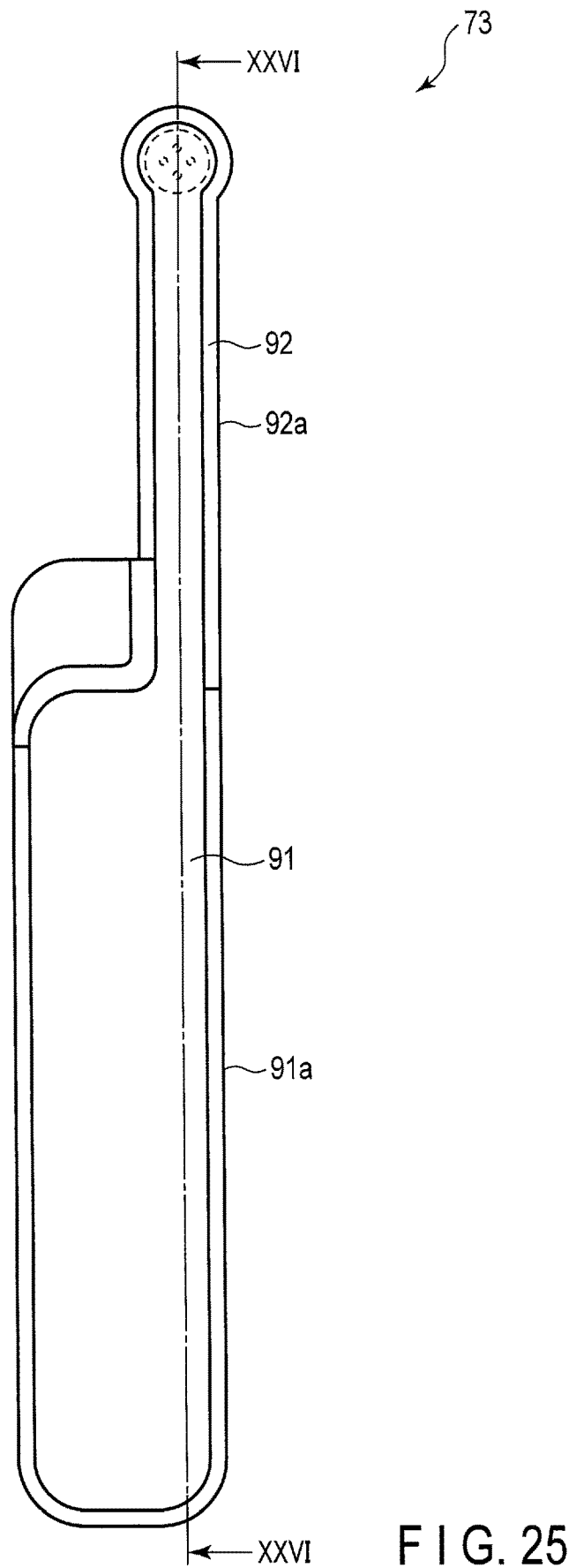
FIG. 25 is a plan view showing a configuration of a sensing cuff of the blood pressure measurement device.
Figure 26:
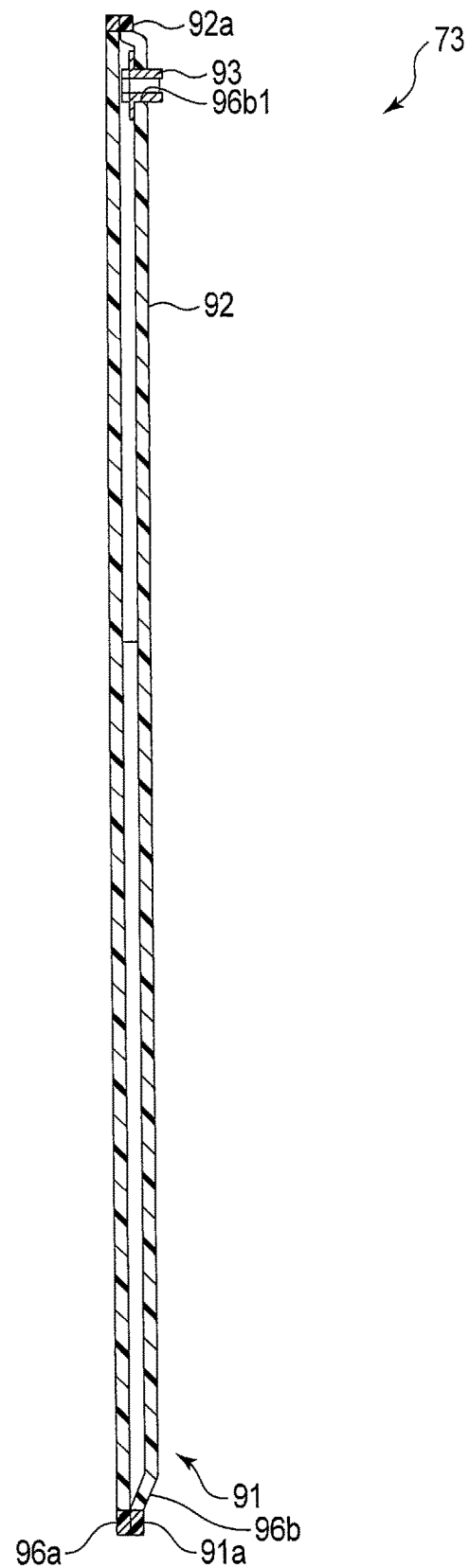
FIG. 26 is a sectional view showing a configuration of the sensing cuff of the blood pressure measurement device.
Figure 29:
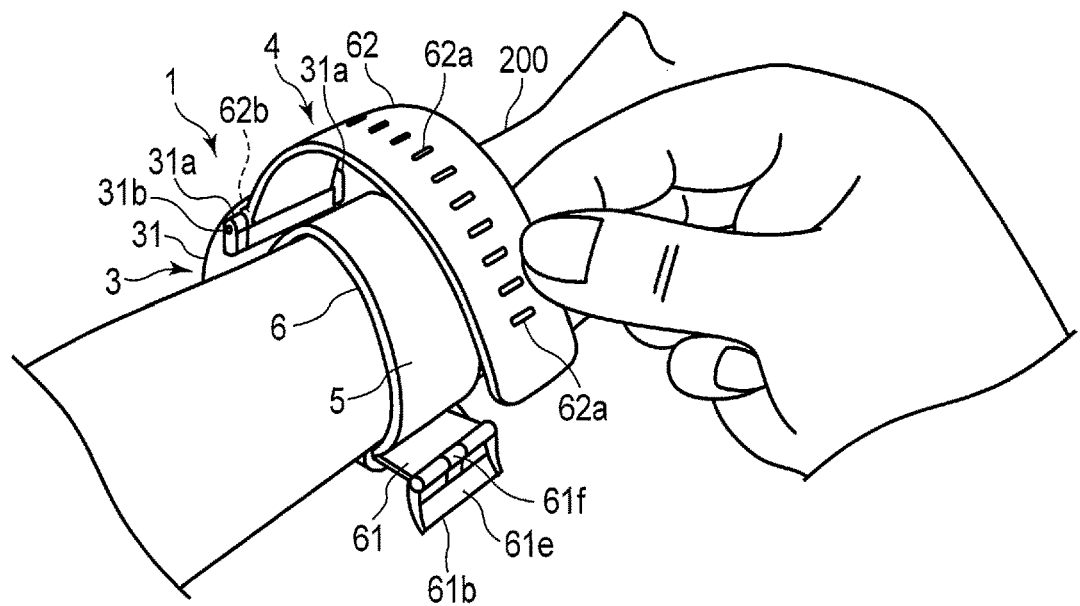
FIG. 29 is a perspective view showing an example of wearing the blood pressure measurement device on the wrist.
Figure 30:
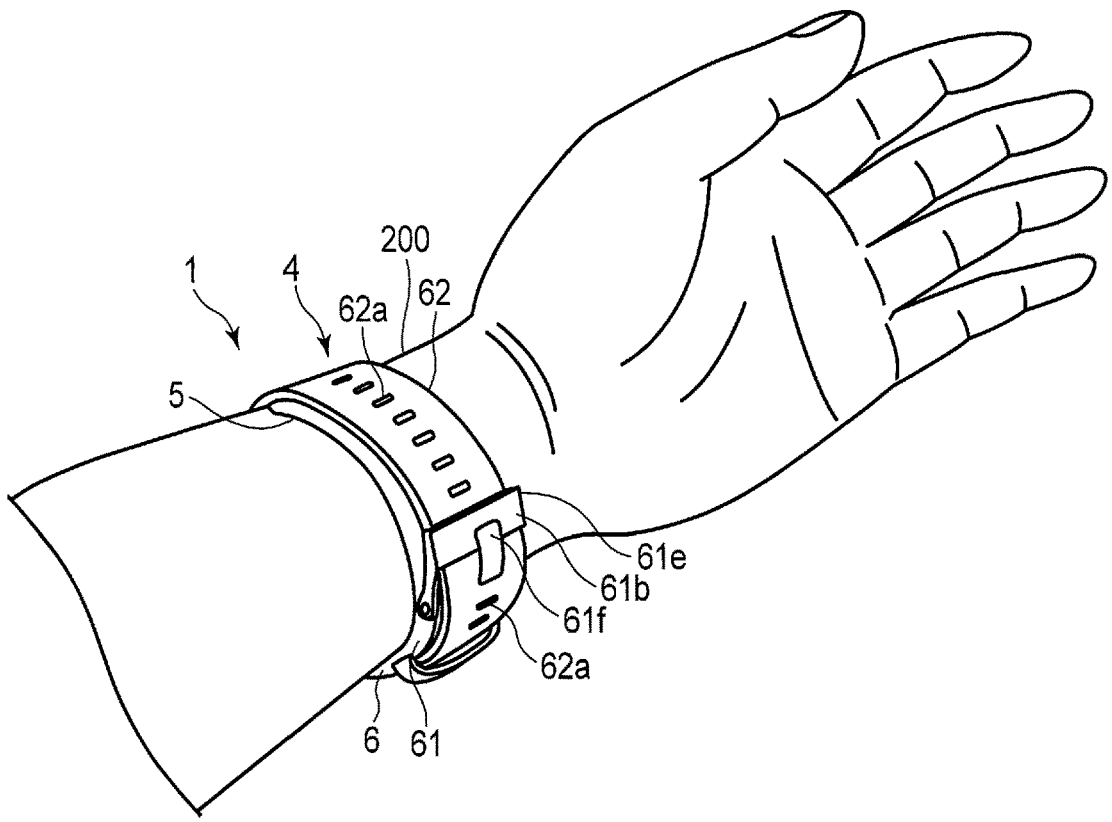
FIG. 30 is a perspective view showing an example of wearing the blood pressure measurement device on the wrist.
Figure 31:
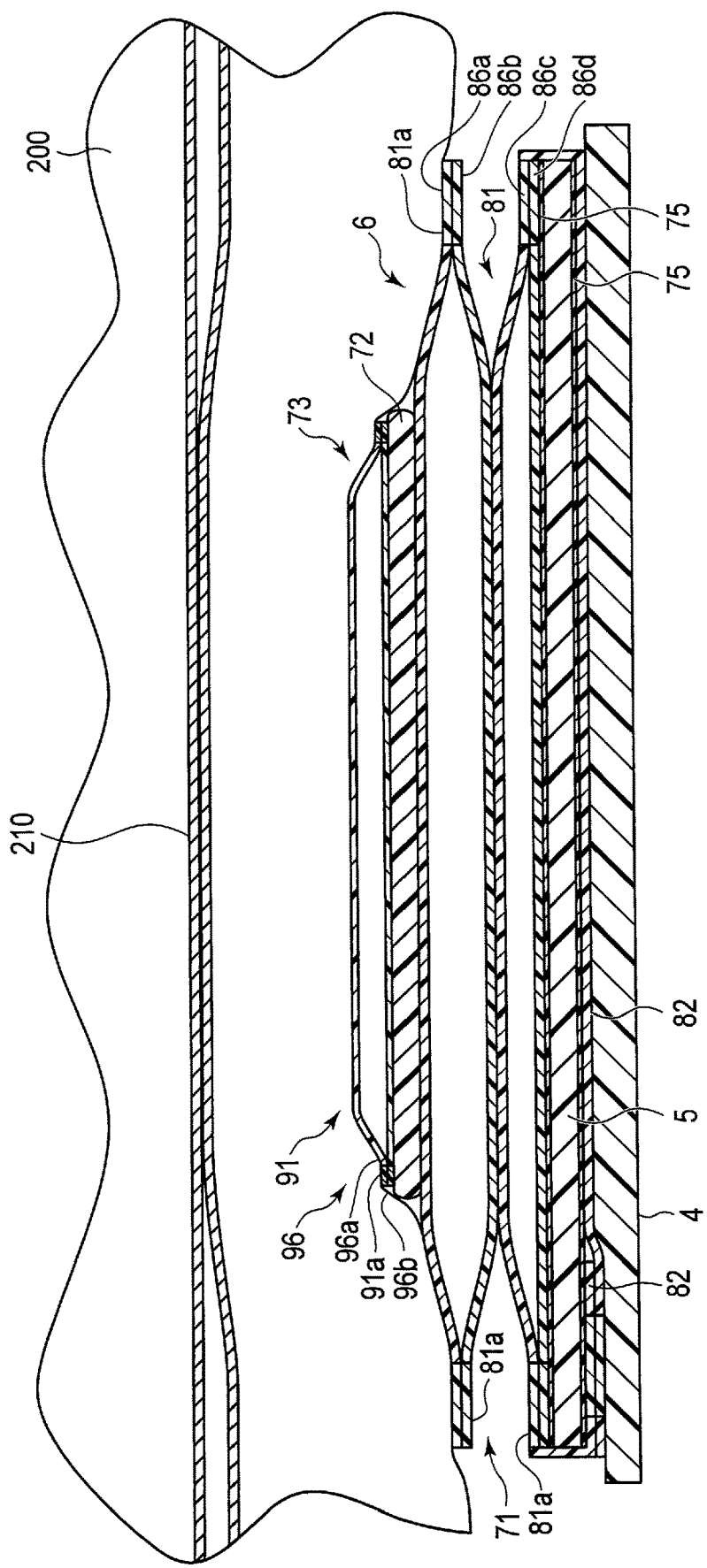
FIG. 31 is a sectional view schematically showing a state in which the blood pressure measurement device is attached to the wrist.

FIG. 25 is a plan view showing a configuration of a sensing cuff 73 of the blood pressure measurement device 1. FIG. 26 is a sectional view showing a configuration of the sensing cuff 73 of the blood pressure measurement device 1 along line XXVI-XXVI in FIG. 25. FIG. 27 is a flowchart showing an example of the use of the blood pressure measurement device 1. FIG. 28 is a perspective view showing an example of wearing the blood pressure measurement device 1 on the wrist 200. FIG. 29 is a perspective view showing an example of wearing the blood pressure measurement device 1 on the wrist 200. FIG. 30 is a perspective view showing an example of wearing the blood pressure measurement device 1 on the wrist 200. FIG. 31 is a sectional view schematically showing a state in which the blood pressure measurement device 1 is attached to the wrist 200.

The blood pressure measurement device 1 is an electronic blood pressure measurement device worn on a living body. The present embodiment will be described, referring to an electronic blood pressure measurement device embodied as a wearable device worn on the wrist 200 of the living body.

As shown in FIGS. 1 to 6, the blood pressure measurement device 1 includes a device body 3, a strap 4 for fixing the device body 3 to the wrist 200, a curler 5 placed between the strap 4 and the wrist 200, a cuff structure 6 including a pressing cuff 71, a sensing cuff 73 and a pulling cuff 74, and a fluid circuit 7 for causing the device body 3 and the cuff structure 6 to continue fluidly, and a power feeding unit 8 provided in the curler 5.

As shown in FIGS. 1 to 5, the device body 3 includes, for example, a case 11, a display unit 12, an operation unit 13, a pump 14, a flow path unit 15, an on-off valve 16, a pressure sensor 17, a power supply unit 18, a vibration motor 19, and a control board 20. The device body 3 supplies fluid to the cuff structure 6 through the pump 14, on-off valve 16, pressure sensor 17, control board 20, and the like.

As shown in FIGS. 1 to 6, the case 11 includes an outer case 31, a windshield 32 that covers an opening of the outer case 31 on the side opposed to (on the outward side of) the wrist 200, a base 33 that is provided closer to the wrist 200 at the interior of the outer case 31, a back cover 35 that covers the side of the outer case 31 closer to the wrist 200, a seal member 36 provided on the undersurface of the back cover 35, and a filter 37.

As shown in FIG. 6, the outer case 31 is formed in a cylindrical shape. The outer case 31 includes a pair of lugs 31a provided at the positions symmetrical in the circumferential direction of the outer surface, and a spring rod 31b provided between the two lugs 31a. In addition, as shown in FIGS. 7 and 11, the end portion on the side of the back cover 35 between the lugs 31a on the outer surface of the outer case 31 is chamfered and formed as a surface inclined with respect to the center line of the outer case 31. The chamfered portion of the outer surface 31f will be defined as a chamfered portion 31h.

As shown in FIGS. 7 and 11, when the strap 4 is worn, it is covered with one end of the strap 4 closer to the case 11 to preventing the chamfered portion 31h from being exposed to the outside. The chamfered portion 31h is formed, for example, into a curved surface having a predetermined gap between the chamfered portion 31h and one end of the strap 4 closer to the outer case 31.

The outer case 31 has a hole 3c through which the inside and outside of the outer case 31 communicate. The hole 31c is formed between the lugs 31a of one pair and the lugs 31a of the other pair. The hole 31c penetrates the outer case 31 in the thickness direction. A plurality of holes 31c, for example, two holes 31c are formed between the lugs 31a. These two holes 31c are arranged side by side in the circumferential direction of the outer case 31.

As shown in FIG. 11, the hole 31c extends linearly. A first opening end 31d of the hole 31c, which is disposed on the inner surface of the outer case 31, is disposed on the outer surface of the outer case 31. The first opening end 31d is disposed at a portion of the inner surface of the outer case 31 between the paired lugs 31a in the circumferential direction. The first opening end 31d is disposed closer to the windshield 32 with respect to a second opening end 31e in the axial direction D of the outer case 31.

The second opening end 31e of the hole 31c, which is disposed on the outer surface of the outer case 31, is located at a portion of the outer surface 31f of the outer case 31 between the paired lugs 31a in the circumferential direction, and also located closer to the wrist 200, in other words, closer to the back cover 35 in the axial direction D of the outer case 31.

In the present embodiment, as one example, the second opening end 31e is disposed in the chamfered portion 31h of the outer surface 31f of the outer case 31. The second opening end 31e of the hole 31c formed between the other paired lugs 31a is opposed to a first strap 61 (described later) of the strap 4 and covered with the first strap 61. The second opening end 31e of the hole 31c formed between the other paired lugs 31a is opposed to a second strap 62 (described later) of the strap 4 and covered with the second strap 62.

The above hole 31c is so formed that its longitudinal direction is inclined with respect to, for example, the center line of the outer case 31. The longitudinal direction of the hole 31c is set to, for example, a direction inclined by 45 degrees from the center line of the outer case 31.

The windshield 32 is, for example, a circular glass plate.

The base 33 holds the display unit 12, operation unit 13, pump 14, on-off valve 16, pressure sensor 17, power supply unit 18, vibration motor 19 and control board 20. In addition, the base 33 is, for example, a part of the flow path unit 15 which causes the pump 14 and the cuff structure 6 to continue fluidly.

The back cover 35 is formed annularly with an opening at the center thereof. The back cover 35 covers the outer peripheral edge of an end portion of the outer case 31 closer to the wrist 200. The back cover 35 is combined integrally with the curler 5 to cover the central opening with the curler 5 and cover the end portion of the outer case 31 closer to the wrist 200 together with the curler 5. Specifically, the back cover 35 is fixed to the curler 5 by four first fastening members 35a and is fixed to the end portion of the outer case 31 closer to the wrist 200 by four second fastening members 35b. The back cover 35 has four hole portions 35c which are provided at the bottom portion and through which the first fastening members 35a fixed to the curler 5 are inserted, and four holes 35d through which the second fastening members 35b, which are fixed to the outer case 31 provided at four portions of the outer surface protruded in the radial direction, are inserted.

The first and second fastening members 35a and 35b are members for mechanically fastening two parts such as screws, bolts and rivets. In the present embodiment, the first and second fastening member 35a and 35b are screws.

The seal member 36 is, for example, a double-sided tape formed in a shape of a region of the back cover 35 which is in contact with the curler 5. The seal member 36 exists between the curler 5 and the back cover 35 to seal a portion between the curler 5 and the back cover 35.

As shown in FIG. 11, the filter 37 is provided at the first opening end 31d of the hole 31c. The filter 37 covers the first opening end 31d. The filter 37 has a function of allowing air to pass and regulating passage of water. Here, regulating passage of water means limiting the amount of water that passes. The filter 37 preferably has the performance of preventing water to pass.

The display unit 12 is placed on the base 33 of the outer case 31 and immediately below the windshield 32. As shown in FIG. 5, the display unit 12 is electrically connected to the control board 20. The display unit 12 is, for example, a liquid crystal display or an organic electroluminescence display. The display unit 12 displays various items of information including date and time and measurement results of blood pressure such as the maximum blood pressure and the minimum blood pressure, a heart rate and the like.

The operation unit 13 is configured to receive a command from a user. For example, as shown in FIG. 5, the operation unit 13 includes a plurality of buttons 41 provided on the case 11, sensors 42 that detect the operations of the buttons 41, and a touch panel 43 provided on the display unit 12 or the windshield 32. The operation unit 13 is operated by the user to convert the command into an electrical signal. The sensors 42 and touch panel 43 are electrically connected to the control board 20 to output the electrical signal to the control board 20.

The number of buttons 41 is, for example, three. The buttons 41 are supported by the base 33 and protrudes from the outer surface of the outer case 31. The buttons 41 and sensors 42 are supported by the base 33. The touch panel 43 is provided integrally with the windshield 32, for example.

As shown in FIG. 9, the pump 14 is, for example, a piezoelectric pump. The pump 14 compresses air and supplies the compressed air to the cuff structure 6 through the flow path unit 15. The pump 14 is electrically connected to the control board 20.

The pump 14 is, for example, formed in a rectangular shape in planar view. The pump 14 has two sides 14a and 14b as end portions. The side 14a is one of the sides of a surface 14c of the pump 14 closer to the windshield 32 and is located closer to the center of the outer case 31 in a direction orthogonal to the axial direction D of the outer case 31. The side 14b is opposed to the side 14a and located closer to the filter 37. The side 14a is, for example, one of the end portions of the pump 14 closer to the center of the outer case 31.

As shown in FIG. 11, the surface 14c of the pump 14 closer to the windshield 32 is located opposite to the first opening end 31d in a direction from one pair of lugs 31a toward the other pair of lugs 31a. As shown in FIG. 9, the pump 14 has a suction hole 14d. The suction hole 14d is formed in the surface 14c. As one example, a plurality of suction holes 14d are provided, and as a specific example, three suction holes are provided. Here, three suction holes 14d will be referred to as a first suction hole 14d1, a second suction hole 14d2 and a third suction hole 14d3.

The pump 14 is located apart from the on-off valve 16 in a direction orthogonal to the axial direction D of the outer case 31 in the outer case 31. The location of the pump 14 in the outer case 31 will be described. Hereinafter, a direction that is parallel to the direction from one pair of lugs 31a to the other pair of lugs 31a will be referred to as a first direction, and a direction that is orthogonal to the first direction and orthogonal to the axial direction D of the outer case 31 will be referred to as a second direction. The pump 14 is disposed closer to the center of the outer case 31 in the second direction and on one side of the outer case 31 from the center thereof in the first direction. As a specific example, the pump 14 is opposed to the filter 37 in the first direction. As one example, the pump 14 is fixed to the base 33 by a double-sided tape. The first suction hole 14d1 is formed near the side 14a and closer to the center in the second directions.

The second suction hole 14d2 is formed closer to the first opening end 31d of the hole 31c in the first direction and on one side in the second direction. The second suction hole 14d2 is formed near one of two sides 14e connecting, for example, the sides 14a and 14b of the surface 14c closer to the windshield 32, and closer to the filter 37 than the center between the sides 14a and 14b.

The third suction hole 14d3 is formed closer to the first opening end 31d of the hole 31c in the first direction and on the other side in the second direction. The third suction hole 14d3 is formed near the other of two sides 14e connecting, for example, the sides 14a and 14b and closer to the filter 37 than the center between the sides 14a and 14b.

As shown in FIG. 5, the flow path unit 15 includes a flow path from the pump 14 to the pressing cuff 71 and pulling cuff 74 and a flow path from the pump 14 to the sensing cuff 73. The flow path unit 15 also includes a flow path from the pressing cuff 71 and pulling cuff 74 to the air and a flow path from the sensing cuff 73 to the air. The flow path unit 15 is an air flow path configured by, for example, a hollow portion, a groove, a flow path tank and a tube which are provided in the base 33 and the like.

The on-off valve 16 opens and closes part of the flow path unit 15. As shown in FIG. 5, as a specific example, four on-off valves 16 are provided and their on-off states are combined to selectively open and close a flow path from the pump 14 to the pressing cuff 71 and pulling cuff 74, a flow path from the pump 14 to the sensing cuff 73, a flow path from the pressing cuff 71 and pulling cuff 74 to the air, and a flow path from the sensing cuff 73 to the air. As a specific example, the four on-off valves 16 include a first on-off valve 16A, a second on-off valve 16B, a third on-off valve 16C and a fourth on-off valve 16D. The first on-off valve 16A opens and closes a flow path connecting the pump 14 and the sensing cuff 73. The second on-off valve 16B opens and closes a flow path connecting the pump 14 and the pulling cuff 74. The second on-off valve 16B and third on-off valve 16C open and close a flow path connecting the pump 14 and the pressing cuff 71. The second on-off valve 16B, third on-off valve 16C and fourth on-off valve 16D open and close a flow path connecting the pump 14 and the air.

As shown in FIGS. 8 to 10, 13 and 14, the first on-off valve 16A, second on-off valve 16B, third on-off valve 16C and fourth on-off valve 16D are disposed apart from the pump 14 and the power supply unit 18 in a direction orthogonal to the axial direction D of the outer case 31. As a specific example, the first on-off valve 16A, second on-off valve 16B, third on-off valve 16C and fourth on-off valve 16D are arranged in the outer case 31 on one side thereof from the center of the outer case 31 in the second direction.

The first on-off valve 16A, second on-off valve 16B, third on-off valve 16C and fourth on-off valve 16D are supported by a support plate 39. The first on-off valve 16A, second on-off valve 16B, third on-off valve 16C and fourth on-off valve 16D, which are supported by the support plate 39, are arranged apart from the pump 14 and the power supply unit 18 in a direction orthogonal to the axial direction D of the outer case 31. In other words, the first on-off valve 16A, second on-off valve 16B, third on-off valve 16C and fourth on-off valve 16D do not overlap the pump 14 or the power supply unit 18 in the axial direction D of the outer case 31. In the present embodiment, as an example, the support plate 39 is also disposed apart from the pump 14 and the power supply unit 18 in a direction orthogonal to the axial direction D of the outer case 31.

The first on-off valve 16A, second on-off valve 16B, third on-off valve 16C and fourth on-off valve 16D are electrically connected to the control board 20.

As an example, the first on-off valve 16A, second on-off valve 16B, third on-off valve 16C and fourth on-off valve 16D are fixed to the surface of the support plate 39 which faces the back cover 35. As an example, the first on-off valve 16A, second on-off valve 16B, third on-off valve 16C and fourth on-off valve 16D are arranged opposite to the buttons 41 with regard to the center of the outer case 31 in the second direction.

The first on-off valve 16A, second on-off valve 16B, third on-off valve 16C and fourth on-off valve 16D so configured are arranged in the order presented from the one-end side to the other-end side closer to the pump 14 in the first direction, as indicated by a dotted line in FIG. 10.

The pressure sensor 17 detects the pressure of at least the sensing cuff 73 as shown in FIG. 5. The pressure sensor 17 includes, for example, a first pressure sensor 17A and a second pressure sensor 17B. The pressure sensor 17 converts the detected pressure into an electrical signal and outputs it to the control board 20. For example, the first pressure sensor 17A and second pressure sensor 17B are provided in a flow path of the flow path unit 15, which connects the first pressure sensor 17A and the sensing cuff 73. The pressure in this flow path corresponds to the pressure of the internal space of the pressing cuff 71, sensing cuff 73 and pulling cuff 74 because the the pump 14 is connected to the pressing cuff 71, sensing cuff 73 and pulling cuff 74 by opening and closing of the on-off valves.

As a specific example, the pressure sensor 17 detects the pressure of the sensing cuff 73, or the pressure of the flow path unit 15 connecting the pump 14 and the sensing cuff 73 when the first on-off valve 16A is open and the second on-off valve 16B is closed. The pressure sensor 17 also detects the pressure of the sensing cuff 73 and pulling cuff 74, or the pressure of the flow path unit 15 connecting the pump 14, sensing cuff 73 and pulling cuff 74 when the first on-off valve 16A and the second on-off valve 16B are open and the third on-off valve 16C is closed. The pressure sensor 17 further detects the pressure of the pressure cuff 71, sensing cuff 73 and pulling cuff 74, or the pressure of the flow path unit 15 connecting the pump 14, pressing cuff 71, sensing cuff 73 and pulling cuff 74 when the first on-off valve 16A, second on-off valve 16B and third on-off valve 16C are open and the fourth on-off valve 16D is open or closed.

The first pressure sensor 17A and second pressure sensor 17B are disposed apart from the pump 14 and the power supply unit 18 in a direction orthogonal to the axial direction D of the outer case 31. In other words, neither the first pressure sensor 17A nor the second pressure sensor 17B overlaps the pump 14 or the power supply unit 18 in the axial direction D of the outer case 31. As a specific example, as shown in FIG. 13, the first pressure sensor 17A and second pressure sensor 17B are supported by, for example, the support plate 39.

The first pressure sensor 17A and second pressure sensor 17B so configured are disposed on the one-end side closer to the pump 14 than the first on-off valve 16A in the first direction, as indicated by the dotted line in FIG. 10. In addition, the first pressure sensor 17A and second pressure sensor 17B are arranged in the order presented from the one-end side to the other-end side closer to the pump 14 in the first direction.

The power supply unit 18 is, for example, a secondary battery such as a lithium-ion battery. As shown in FIG. 5, the power supply unit 18 is electrically connected to the control board 20. The power supply unit 18 supplies power to the control board 20.

The power supply unit 18 is fixed to the surface 18a of the pump 14 which faces the windshield 32. The power supply unit 18 is formed in a long shape in one direction and, as an example, it is formed in a rectangular parallelepiped shape. As shown in FIGS. 8 and 9, the length of the power supply unit 18 in its widthwise direction is substantially the same as the length of the pump 14 along the widthwise direction of the power supply unit 18 in a state where the power supply unit 18 is fixed to the pump 14. In other words, the width of the power supply unit 18 is substantially the same as the width of the pump 14 along the second direction.

The longitudinal direction of the power supply unit 18 is along the first direction, and the one-end side in the longitudinal direction is opposed to the pump 14. The fact that the one-end side is opposed to the pump 14 includes the facts that "the center of the pump 14 in its longitudinal direction is opposed to the side 14a of the pump 14, which corresponds to an end portion closer to the center of the case 11, in the axial direction D of the outer case 31 and the vicinity of the center of the case 11 of the pump 14 is opposed to the side 14a of the pump 14, which corresponds to an end portion closer to the center of the case 11. In addition, the power supply unit 18 is disposed such that, for example, the center of the power supply unit 18 in its widthwise direction is opposed to the center of the pump 14 in the second direction.

As shown in FIG. 9, the power supply unit 18 is fixed by double-sided tapes 38 to the side 14a of the surface 14c of the pump 14, which faces the windshield 32, the side 14a being an end portion closer to the center of the case 11. The double-sided tapes 38 are provided at both end portions of the surface 14c of the pump 14 in the second direction. Note that one of the double-sided tapes 38 is placed closer to the side 14a than the second suction hole 14d2 formed in the surface 14c of the pump 14. The other double-sided tape 38 is placed closer to the side 14a than the third suction hole 14d3 formed in the surface 14c. The double-sided tapes 38 are each formed in a strap shape along the first direction.

One side of the above-described power supply unit 18 in its longitudinal direction is opposed to the pump 14 in the axial direction D of the outer case 31. The other side thereof in the longitudinal direction is closer to the windshield 32 with respect to the control board 20 in the axial direction D of the outer case 31. A wiring line connecting the power supply unit 18 and the control board 20 is disposed at one end of the power supply unit 18 closer to the control board 20 in the longitudinal direction.

As shown in FIG. 11, the double-sided tape 38 is provided between the power supply unit 18 and the pump 14 to fix the pump 14 and the power supply unit 18. The double-sided tapes 38 create a gap S, which corresponds to the thickness of the double-sided tapes 38, between the pump 14 and the power supply unit 18. The gap S is opposed to the first opening end 31d of the hole 31c with the filter 37 therebetween in the first direction. In other words, the gap S is flush with part of the first opening end 31d in the axial direction D of the outer case 31.

As shown in FIG. 5, the control board 20 includes, for example, a board 51, an acceleration sensor 52, a communication unit 53, a storage unit 54 and a control unit 55. The control board 20 is configured by mounting the acceleration sensor 52, communication unit 53, storage unit 54 and control unit 55 on the board 51.

The board 51 is fixed to the base 33 of the case 11 by screws or the like.

The acceleration sensor 52 is, for example, a 3-axis acceleration sensor. The acceleration sensor 52 supplies the control unit 55 with an acceleration signal representing the acceleration of the device body 3 in three directions which are orthogonal to each other. For example, the acceleration sensor 52 is used to measure, from the detected acceleration, the activity amount of a living body equipped with the blood pressure measurement device 1.

The communication unit 53 is configured to transmit and receive information to and from an external device by radio or wire. The communication unit 53 transmits, for example, information controlled by the control unit 55 and information on the measured blood pressure value and pulse and the like to an external device via a network, and also receives, for example, a software update program from the external device via the network and transmits it to the control unit.

In the present embodiment, the network is, for example, the Internet; however, it is not limited to the Internet but may be a network such as a local area network (LAN) provided in a hospital or may be direct communication with an external device using a cable having a terminal of a predetermined standard such as a USB. For this reason, the communication unit 53 may include a plurality of wireless antennas and micro USB connectors, and the like.

The storage unit 54 stores in advance program data for controlling the entire blood pressure measurement device 1 and the fluid circuit 7, setting data for setting various functions of the blood pressure measurement device 1, calculation data for calculating a blood pressure value and a pulse from the pressure measured by the pressure sensor 17, and the like. The storage unit 54 also stores information on the measured blood pressure value and pulse, and the like.

The control unit 55 is configured by one or more CPUs to control the operation of the entire blood pressure measurement device 1 and the operation of the fluid circuit 7. The control unit 55 is electrically connected to the display unit 12, operation unit 13, pump 14, on-off valve 16 and pressure sensor 17 to apply power thereto. The control unit 55 also controls the operations of the display unit 12, pump 14 and on-off valve 16 based on the electrical signals output from the operation unit 13 and the pressure sensor 17.

For example, as shown in FIG. 5, the control unit 55 includes a main central processing unit (CPU) 56 for controlling the operation of the entire blood pressure measurement device 1 and a sub-CPU 57 for controlling the operation of the fluid circuit 7. For example, the main CPU 56 obtains the measurement results of blood pressure values such as the maximum blood pressure and the minimum blood pressure and heart rates from the electric signal output from the pressure sensor 17, and outputs an image signal corresponding to the measurement results to the display unit 12.

For example, upon receiving a command for measuring blood pressure from the operation unit 13, the sub-CPU 57 drives the pump 14 and the on-off valve 16 to send compressed air to the pressing cuff 71 and sensing cuff 73. The sub-CPU 57 also controls the start and stop of the pump 14 and the opening and closing of the on-off valve 16 based on the electrical signal output from the pressure sensor 17. The sub-CPU 57 controls the pump 14 and the on-off valve 16 to send compressed air selectively to the pressing cuff 71 and the sensing cuff 73 and to selectively depressurize the pressing cuff 71 and the sensing cuff 73.

As shown in FIG. 9, the control board 20 so configured is placed apart from the pump 14, first on-off valve 16A, second on-off valve 16B, third on-off valve 16C, fourth on-off valve 16D, first pressure sensor 17A and second pressure sensor 17B in a direction orthogonal to the axial direction D of the outer case 31. Specifically, the control board 20 is placed apart from the pump 14 in the first direction placed apart from the first on-off valve 16A, second on-off valve 16B, third on-off valve 16C, fourth on-off valve 16D, first pressure sensor 17A and second pressure sensor 17B in the second direction. The control board 20 is fixed to the base 33 by an adhesive tape, for example.

As shown in FIGS. 1 to 4, the strap 4 includes a first strap 61 provided on one pair of lugs 31a and the spring rod 31b and a second strap 62 provided on the other pair of lugs 31a and the spring rod 31b. The strap 4 is wound around the wrist 200 with the curler 5 therebetween.

The first strap 61 is what is called a parent, and is formed like a strap connectable to the second strap 62. As shown in FIGS. 1 to 3, the first strap 61 includes a strap portion 61a and a buckle 61b. The strap portion 61a is formed like a strap. The strap portion 61a is formed of an elastically deformable resin material. In addition, the strap portion 61a has a sheet-like insert member which is flexible and which prevents the strap portion 61a from expanding/contracting in the longitudinal direction. The strap portion 61a has a first hole portion 61c which is formed in at one end and orthogonal to the longitudinal direction of the strap portion 61a and a second hole portion 61d which is formed at the other end and which is orthogonal to the longitudinal direction of the first strap 61.

As shown in FIG. 4, the first hole portion 61c is provided at an end portion of the strap portion 61a. The first hole portion 61c can receive the spring rod 31b inserted thereinto and has an inner diameter permitting the first strap 61 to rotate with respect to the spring rod 31b. That is, the first strap 61 is rotatably held by the outer case 31 between the paired lugs 31a and with the spring rod 31b being within the first hole portion 61c.

As shown in FIGS. 1 and 3, the second hole portion 61d is provided at the distal end of the strap portion 61a. The buckle 61b is attached to the second hole portion 61c. One end of the strap portion 61a so formed, which is closer to the case 11, is opposed to the chamfered portion 31h of the outer case 31.

As shown in FIGS. 1 and 3, the buckle 61b includes a rectangular frame-shaped body 61e and a stick 61f rotatably attached to the frame-shaped body 61e. One side of the frame-shaped body 61e, to which the stick 61f is attached, is inserted into the second hole portion 61d and is rotatably attached to the strap portion 61a.

The second strap 62 is referred to as a sword tip and is formed in a strap shape with a width that enables the second strap to be inserted into the frame-shaped body 61e. The second strap 62 is formed of an elastically deformable resin material. The second strap 62 has a sheet-like insert member which is flexible and which prevents the second strap 62 from expanding/contracting in the longitudinal direction.

As shown in FIGS. 1 and 2, the second strap 62 has a plurality of small holes 62a into which the stick 61f is inserted. The second strap 62 has a third hole portion 62b provided at one end portion and being orthogonal to the longitudinal direction of the second strap 62. The third hole portion 62b can receive the spring rod 31b inserted thereinto and has an inner diameter permitting the second strap 62 to rotate with respect to the spring rod 31b. That is, the second strap 62 is rotatably held by the outer case 31 between the paired lugs 31a and with the spring rod 31b being within the third hole portion 62b.

One end of the second strap 62 thus configured, which is closer to the case 11, is opposed to the chamfered portion 31h of the outer case 31.

In the strap 4 described above, the second strap 62 is inserted into the frame-shaped body 61e and the stick 61f is inserted into a small hole 62a, with the result that the first strap 61 and the second strap 62 are integrally connected, and together with the outer case 31, form an annular shape conformable to the wrist 200 of a user in the circumferential direction. Since the strap 4 is formed in an annular shape, the curler 5 is pressed and elastically deformed to conform to the wrist 200 of a user of the blood pressure measurement device 1 in the circumferential direction.

As shown in FIGS. 1 to 4, the curler 5 is formed like a strap curving along the circumferential direction of the wrist 200. The curler 5 is also formed such that one end and the other end are separated from each other. For example, the outer surface of the curler 5 at one end is fixed to the back cover 35 of the device body 3. One end and the other end of the curler 5 project toward one side of the wrist 200 rather than toward the back cover 35. Thus, when the blood pressure measurement device 1 is attached to the wrist 200, one end and the other end of the curler 5 are located on the side of the wrist 200. In addition, one end and the other end of the curler 5 are adjacent to each other with a predetermined distance therebetween. The curler 5 is formed of, for example, a resin material. As a specific example, the curler 5 is formed of polypropylene with a thickness of about 1 mm.

As a specific example, as shown in FIGS. 1 to 4, the curler 5 is formed in a strap-like shape curved along the circumferential direction of the wrist 200. The curler 5 includes a disk-shaped cover portion 5a provided at a position opposite to the back of the hand of the wrist 200 on one end side and a clearance portion 5b provided around the cover portion 5a and capable of moving the second fastening members 35b for fixing the outer case 35 and the back cover 35. The disk-shaped cover portion 5a constitutes a back lid together with the back cover 3.

The curler 5 is formed, for example, in such a manner that the cover portion 5a and its adjacent portion are formed in a flat plate shape, and the one end and other end of the curler 5 are curved at a predetermined curvature more than the cover portion 5a. The curler 5 is so formed that the length from the cover portion 5a to one end is shorter than the length from the cover portion 5a to the other end. As a specific example, the shorter side of the curler 5 from the cover portion 5a to one end is placed on the back of the hand of the wrist 200, and the longer side thereof from the cover portion 5a to the other end extends from the back of the hand of the wrist 200 to the palm of the hand of the wrist 200 through one side.

As shown in FIG. 20, the curler 5 is so formed that when one end and the other end are close to each other, the other end is located on the inner surface side on the one end side. As a specific example, the width of the curler 5 in the width direction of the wrist 200 is set larger on the back side of the wrist 200 of the curler 5 than on the palm side of the wrist 200 of the curler 5. In the curler 5, the radius of curvature of one end on the back side of the wrist 200 is set larger than that of the other end on the palm side of the wrist 200. With this configuration, when both ends of the curler 5 abut on each other, the other end is disposed more inwardly in the curler 5 than one end. In the curler 5, a recess 5c is provided adjacent to the cover portion 5a in part of the cover portion 5a, the outer surface on the one end side from the cover portion 5a, and the outer surface extending in the widthwise direction from the cover portion 5a.

The cover portion 5a includes an inserted reinforcing insert member 5d. The cover portion 5a is fixed to the outer case 31 on the wrist 200 side through the fixed back cover 35. The cover portion 5a includes a screw hole 5e which faces the four hole portions 35c of the back cover 35 and into which the first fastening member 35a for fixing the back cover 35 is screwed, and a three hole portion 5f for connecting the cuff structure 6 to the device body 3. The screw hole 5e into which the first fastening member 35a for fixing the back cover 35 is screwed.

The clearance portion 5b is a clearance for placing the first fastening member 35a on the back cover 35 without interfering with the curler 5 by the second fastening member 35b and for arranging tools that rotate the second fastening member 35b when the back cover 35 is fixed to the outer case 31 from the back cover 35 side by the second fastening member 35b.

The three hole portions 5f are a first hole portion 5f1 formed to have an inner diameter into which a connecting portion 84 (described later) of the pressing cuff 71 can be inserted, a second hole portion 5f2 formed to have an inner diameter into which a connecting portion 93 (described later) of the sensing cuff 73 can be inserted, and a third hole portion 5f3 formed to have an inner diameter into which a connecting portion 103 (described later) of the pulling cuff 74 can be inserted. In the present embodiment, the second hole portion 5f2 is disposed closer to the other end of the curler 5 on the palm side in the cover portion 5a than the first and third hole portions 5f1 and 5f3.

The curler 5 is fixed to the outer case 31 such that one end and the other end are opposed to the second strap 62 of the strap 4. The curler 5 is curved along the circumferential direction of the wrist 200 on the palm side to hold the cuff structure 6 opposed to the palm side of the wrist 200 in a curved state following the shape of the palm side of the wrist 200.

The curler 5 has such hardness as provides both flexibility and shape retention. For example, the flexibility described here means that the shape of the curler 5 is deformed in the radial direction when the external force of the strap 4 is applied to the curler 5. For example, when the curler 5 is pressed by the strap 4, the curler 5 moves closer to the wrist 200, or the shape of the curler 5 becomes similar to that of the wrist 200 or moves in conformity with the shape of the wrist 200 in a side view. For example, the shape retention means that the curler 5 can maintain a pre-fabricated shape when an external force is not applied, and in the present embodiment, the shape of the curler 5 can maintain a shape that curves along the circumferential direction of the wrist 200.

The cuff structure 6 is disposed on the inner surface of the curler 5, and the cuff structure 6 is held along the shape of the inner surface of the curler 5. As a specific example, the pressing cuff 71 and the pulling cuff 74 are disposed on the inner surface of the curler 5, and the cuff structure 6 is fixed and held by a bonding layer 75 provided between the pressing cuff 71 and the pulling cuff 74. In the present embodiment, the bonding layer 75 is an adhesive and a double-sided tape.

As shown in FIGS. 1 to 3, 15, 21 and 22, the cuff structure 6 includes a pressing cuff 71, a back plate 72, a sensing cuff 73 and a pulling cuff 74. The cuff structure 6 includes a bonding layer 75 for bonding respective structures and for bonding the curler 5 and the cuffs 71 and 74. The cuff structure 6 is fixed to the curler 5. In the cuff structure 6, the pressing cuff 71, back plate 72 and sensing cuff 73 are stacked and placed on the curler 5, and the pulling cuff 74 is placed on the curler 5 apart from the pressing cuff 71, back plate 72 and sensing cuff 73.

As a specific example, as shown in FIG. 4, the cuff structure 6 is fixed to the palm side inner surface of the curler 5 on the wrist 200 by stacking the pressing cuff 71, back plate 72 and sensing cuff 73 in this order from the inner surface of the curler 5 toward the wrist. In the cuff structure 6, the pulling cuff 74 is placed on the back side inner surface of the curler 5 on the wrist 200. Each member of the cuff structure 6 is fixed to its adjacent members in the stacking direction by a bonding layer 75.

The pressing cuff 71 is fluidly connected to the pump 14 through the flow path unit 15. The pressing cuff 71 inflates and presses the back plate 72 and the sensing cuff 73 against the wrist 200. As shown in FIGS. 15 to 17, the pressing cuff 71 includes a plurality of air bag 81 of, for example, two layers, a to-be-bonded portion 82, which is provided in the air bags 81 opposite to the curler 5, a flow path body 83 communicating with the air bags 81, and a connecting portion 84 provided at the distal end of the flow path body 83. The pressing cuff 71 is configured by welding a plurality of sheet members 86 integrally to each other.

The air bags 81 have a bag-shaped structure. The present invention will be described using the air bags because the blood pressure measurement device 1 is configured to use air supplied by the pump 14. When a fluid other than air is used, the bag-shaped structure may be a fluid bag inflated by the fluid. The air bags 81 are stacked and fluidly communicate in their stacking direction.

The air bags 81 are formed in a rectangular bag shape elongated in one direction. The width of each of the air bags 81 in its widthwise direction is set to the same as the width of the curler 5 in its widthwise direction. The air bags 81 are each formed, for example, by combining two sheet members 86 and welding them at a welding portion 81a by heat in a rectangular frame shape elongated in one direction, as shown in FIGS. 21 to 24. Each of the air bags 81 of two layers is formed by integrally combining two air bags 81 by welding by heat, or by welding opposing sheet members 86 of adjacent air bags 81 and then welding the air bags 81 to the welded sheet members 86. As a specific example, the air bags 81 of two layers fluidly continuous through openings provided in the sheet members 86 opposed to each other. In the air bags 81 of two layers, the opposing sheet members 86 are bridge-welded to each other in a four-sided frame shape that is smaller than the welding portion 81a located on the outer peripheral edge, and a plurality of openings are surrounded with a bridge welding portion 81b, with the result that adjacent air bags 81 are formed integrally and are fluidly continuous at the interior of the bridge welding portion 81b. Here, the bridge welding and the bridge of the welding portion 81b mean bonding adjacent air bags 81 integrally with each other.

One or more to-be-bonded portions 82 are provided on at least part of an edge portion of the air bags 81 placed adjacently to the curler 5. The to-be-bonded portions 82 are formed of part of the sheet members 86 that constitute the air bags 81.

The present embodiment is directed to a case where one to-be-bonded portion 82 is provided at each of the edge portions of the air bag 81 in its widthwise direction, as shown in FIGS. 15 to 17 and 21 to 24. Note that for example, the to-be-bonded portion 82 may be divided in the longitudinal direction of the air bag 81 by a slit, or a plurality of to-be-bonded portions may be provided in the longitudinal direction of the air bag 81. When the pressing cuff 71 is placed on the inner surface of the curler 5, the to-be-bonded portion 82 is bonded at least to the outer surface of the curler 5. In addition, for example, two to-be-bonded portions 82 are stacked and welded.

Note that the two to-be-bonded portions 82 are set to have different lengths, for example, in the widthwise direction of the air bag 81. In this example, the two to-be-bonded portions 82 are stacked and welded at one end of the curler 5 in the widthwise direction. Note that the length of the two to-be-bonded portions 82 can appropriately be set and they may be stacked or not if their distal ends can be disposed on the outer surface of the curler 5. When the length is set such that the two to-be-bonded portions can be stacked, the distal ends are preferably not extended outward beyond the outer edge of the outer surface of the curler 5.

As shown in FIGS. 15 to 18, the flow path body 83 is provided integrally with part of a longitudinal-direction one edge of one of the air bags 81, e.g., the air bag 81 adjacent to the curler 5. As a specific example, the flow path body 83 is provided at an end of the air bag 81 close to the device body 3. The flow path body 83 is formed in a shape elongated in one direction with a width smaller than that of the air bag 81 in its widthwise direction, and its distal end is formed in a circular shape. The flow path body 83 has a connecting portion 84 at the distal end thereof. The flow path body 83 is connected to the flow path unit 15 through the connecting portion 84 to form a flow path between the air bag 81 and the flow path unit 15 of the device body 3.

The flow path body 83 is configured by welding part of a sheet member 86 adjacent to an area of the air bag 81 of the sheet member 86 by heat in a frame shape elongated in one direction, with the connecting portion 84 placed in the two sheet members 86. The flow path body 83 is interposed between the inner surface of the curler 5 and the pulling cuff 74, and its distal end is located on the wrist 200 side main surface of an area where the cover portion 5a of the curler 5 is provided, and at a position opposed to the first hole portion 5f1. The width of the flow path body 83 excluding a welded portion 83a is, for example, 3.8 mm.

The air bag 81 provided with the flow path body 83 is fluidly continuous with the flow path body 83 by not welding part of the welding portion 81a for welding two sheet members 86 in a rectangular frame shape to be continuous with the welding portion 83a that constitutes the flow path body 83.

The connecting portion 84 is, for example, a nipple. The connection portion 84 is provided at the distal end of the flow path body 83. The distal end of the connecting portion 84 is exposed from one of the two sheet members 86 of the flow path body 83, which is opposed to the curler 5. The connecting portion 84 is inserted into the first hole portion 5f1 of the curler 5 and connected to the flow path unit 15.

As a specific example, as shown in FIGS. 16 and 17, the pressing cuff 71 includes, from the wrist 200 side, a first sheet member 86a, a second sheet member 86b forming the first-layer air bag 81 together with the first sheet member 86a, a third sheet member 86c integrally bonded to the second sheet member 86b to form a to-be-bonded portion 82, and a fourth sheet member 86d forming a second-layer air bag 81 and a flow path body 83 together with the third sheet member 86c. Note that the pressing cuff 71 is formed integrally with its adjacent sheet members 86 by welding by heat.

The first sheet member 86a and the second sheet member 86b are formed in a rectangular shape like the air bags 81, and the peripheral edge portions of the four sides thereof are welded to form the air bags 81. The second sheet member 86b and the third sheet member 86c are opposed to each other, and each include a plurality of openings 86b1 and 86c1 that make the two air bags 81 fluidly continuous with each other. The second sheet member 86b and the third sheet member 86c are formed integrally with each other by welding the peripheries of the openings 86b1 and 86c1 by heat into a four-sided frame shape that is smaller than four sides to which the air bags 81 are welded.

The third sheet member 86c is formed in a shape capable of configuring, for example, the air bags 81, to-be-bonded portions 82 and flow path body 83. The fourth sheet member 86d is formed in a shape capable of configuring, for example, the air bags 81 and flow path body 83. The fourth sheet member 86d has, for example, a hole portion 86d1 into which the distal end of the connecting portion 84 can be inserted.

The third sheet member 86c and the fourth sheet member 86d are opposed to each other, and are welded by heat along the peripheral edges of the air bags 81 and the flow path body 83 and cut in a predetermined shape so that the air bags 81 and the flow path body 83 are fluidly continuous with each other, thus forming the air bags 81, to-be-bonded portions 82 and flow path body 83.

In the fourth sheet member 86d, the connecting portion 84 is placed in a hole portion 86d1, and the periphery of the hole portion 86d1 is welded to the connecting portion 84 by heat. Furthermore, the fourth sheet member 86d is bonded to the inner surface of the curler 5 through the bonding layer 75. The to-be-bonded portions 82 of the third sheet member 86c are bonded to the outer surface of the curler 5 through the bonding layer 75.

As shown in FIGS. 16 and 17, the back plate 72 is bonded to the outer surface of the first sheet member 86a of the pressing cuff 71 with the bonding layer 75. The back plate 72 is formed of a resin material and in a plate shape. The back plate 72 is formed of, for example, polypropylene and is formed in a plate shape having a thickness of approximately 1 mm. The back plate 72 has a shape following property.

The shape-following property described here refers to a function in which the back plate 72 can be deformed in conformity with the shape of the contacted portion of the wrist 200 to be placed, and the contacted portion of the wrist 200 is a portion of the wrist 200 opposed to the back plate 72. The contact described here includes both direct contact and indirect contact with the sensing cuff 73.

For example, as shown in FIG. 17, the back plate 72 has a plurality of grooves 72a on both major surfaces thereof to extend in a direction orthogonal to the longitudinal direction of the back plate 72. As shown in FIG. 17, a plurality of grooves 72a are provided on each of the major surface of the back plate 72. The grooves 72a provided on both major surfaces are opposed to each other in the thickness direction of the back plate 72. The grooves 72a are also arranged at equal intervals in the longitudinal direction of the back plate 72.

Since the back plate 72 is thinner at portions where the grooves 72a are provided than at portions where no grooves are provided, the portions where the grooves 72a are provided are easily deformable. Thus, the back plate 72 has a shape-following property in which the back plate 72 is deformed in accordance with the shape of the wrist 200 and extends in the circumferential direction of the wrist 200. The back plate 72 has a length that covers the palm side of the wrist 200. The back plate 72 transmits a pressing force from the pressing cuff 71 to the back plate 72 side major surface of the sensing cuff 73 while conforming to the shape of the wrist 200.

The sensing cuff 73 is fluidly connected to the pump 14 through the flow path unit 15. The sensing cuff 73 is fixed to the wrist 200 side major surface of the back plate 72. As shown in FIGS. 4 and 16, the sensing cuff 73 is brought into direct contact with that a region of the wrist 200 where the artery 210 exists. The artery 210 is a radial artery and a ulnar artery. The sensing cuff 73 is formed to have the same shape as the back plate 72 or to have a shape smaller than the back plate 72 in the longitudinal direction and width direction of the back plate 72. When the sensing cuff 73 is inflated, it presses the region where the palm side artery 210 of the wrist 200 is present. The sensing cuff 73 is pressed against the wrist 200 by the inflated pressing cuff 71 with the back plate 72 therebetween.

As a specific example, as shown in FIGS. 16, 17, 25 and 26, the sensing cuff 73 includes one air bag 91, a flow path body 92 that communicates with the air bag 91, and a connecting portion 93 provided at the distal end of the flow path body 92. The sensing cuff 73 has one major surface of the air bag 91 fixed to the back plate 72. For example, the sensing cuff 73 is bonded to the wrist 200 side major surface of the back plate 72. This sensing cuff 73 is formed by welding two sheet members 96 integrally with each other.

The air bag 91 is a bag-shaped structure. Since the blood pressure measurement device 1 of the present embodiment is configured to use air supplied by the pump 14, a description will be given of the air bag. When a fluid other than air is used, the bag-shaped structure may be a liquid bag that is inflated by the fluid.

The air bag 91 is formed in a rectangular shape elongated in one direction. For example, the air bag 91 is formed by combining two sheet members 96 that are elongated in one direction and welding them by heat like a rectangular frame elongated in one direction as a welding portion 91a is shown in FIGS. 16, 17, 21, 25 and 26. In addition, the air bag 91 includes, for example, a bonding margin 91b to secure an area for bonding the air bag 91 to the back plate 72 using the bonding layer 75. The bonding margin 91b is formed of, for example, a sheet member 96 opposed to the back plate 72.

The flow path body 92 is provided integrally with part of one longitudinal-direction edge of the air bag 91. As a specific example, the flow path body 92 is provided at that end portion of the air bag 91 which is close to the device body 3. The flow path body 92 is formed in a shape elongated in one direction with a width smaller than that of the air bag 91 in its widthwise direction, and its distal end is formed in a circular shape. The flow path body 92 has a connecting portion 93 at the distal end thereof. The flow path body 92 has a connecting portion 93 at the distal end thereof. The flow path body 92 is connected to the flow path unit 15 through the connecting portion 93 to form a flow path between the air bag 91 and the flow path unit 15 of the device body 3.

The flow path body 92 is configured by welding part of a sheet member 96 adjacent to an area of the air bag 91 of the sheet member 96 by heat in a frame shape elongated in one direction, with the connecting portion 93 placed in the two sheet members 96. The air bag 91 is fluidly continuous with the flow path body 92 by not welding part of the welding portion 91a for welding two sheet members 96 in a rectangular frame shape to be continuous with the welding portion 92a that constitutes the flow path body 92. The flow path body 92 is interposed between the inner surface of the curler 5 and the pulling cuff 74, and its distal end is located on the wrist 200 side main surface of an area where the cover portion 5a of the curler 5 is provided, and at a position opposed to the second hole portion 5f2. The width of the flow path body 92 excluding a welded portion 92a is, for example, 3.8 mm.

The connecting portion 93 is, for example, a nipple. The connection portion 93 is provided at the distal end of the flow path body 92. The distal end of the connecting portion 93 is exposed outward from one of the two sheet members 96 of the flow path body 92, which is opposed to the curler 5 and back plate 72. The connecting portion 93 is inserted into the second hole portion 5f2 of the curler 5 and connected to the flow path unit 15.

As a specific example, as shown in FIGS. 16 and 17, the sensing cuff 73 includes, from the wrist 200 side, a fifth sheet member 96a and a sixth sheet member 96b. Note that the sensing cuff 73 is formed by welding and bonding adjacent sheet members 96 together by heat.

For example, the fifth sheet member 96a and the sixth sheet member 96b are configured in a shape capable of forming the air bag 91, bonding margin 91b and flow path body 92. The fifth sheet member 96a and the sixth sheet member 96b are opposed to each other, and are welded by heat along the peripheral edges of the air bag 91 and the flow path body 92 and cut in a predetermined shape so that the air bag 91 and the flow path body 92 are fluidly continuous with each other, thus forming the air bag 91 and the flow path body 92.

The sixth sheet member 96b has, for example, a hole portion 96b1 into which the distal end of the connecting portion 93 can be inserted. In the sixth sheet member 96b, the connecting portion 93 is placed in the hole portion 96b1, and the periphery of the hole portion 96b1 is welded to the connecting portion 93 by heat. The sixth sheet member 96b is bonded to the inner surface of the back plate 72 through the bonding layer 75.

The pulling cuff 74 is fluidly connected to the pump 14 via the flow path unit 15. The pulling cuff 74 is inflated to press the curler 5 so as to separate from the wrist 200 and thus to pull the strap 4 and the curler 5 toward the back side of the hand of the wrist 200. The pulling cuff 74 includes a plurality of air bags 101 of, for example, six layers, a to-be-bonded portion 102 provided in the air bag 101 opposed to the curler 5, a connecting portion 103 provided in the air bag 101 opposed to the curler 5, and a notch 104 provided at least in the air bag 101 opposed to the curler 5. The pulling cuff 74 is configured by integrally welding a plurality of sheet members 106. The pulling cuff 74 is fixed to an area where the flow path bodies 83 and 92 are provided and to the back side of the hand of the wrist 200 of the curler 5 including the cover portion 5a. That is, the flow path body 83 of the pressing cuff 71 and the flow path body 92 of the sensing cuff 73 are arranged between the pulling cuff 74 and the back side of the hand of the wrist 200 of the curler 5.

In addition, the thickness of the inflated pulling cuff 74 is larger than that of the inflated pressing cuff 71 and that of the inflated sensing cuff 73 in the inflation direction and, in the present embodiment, in a direction opposite to the curler 5 and the wrist 200. That is, the air bag 101 of the pulling cuff 74 has a layer structure including more layers than the air bag 81 of the pressing cuff 71 and the air bag 91 of the sensing cuff 73, and the pulling cuff 74 inflated from the curler 5 toward the wrist 200 is thicker than the pressing cuff 71 and the sensing cuff 73.

In the present embodiment, the pulling cuff 74 including a six-layer air bag 101 includes a first outer layer 111 composed of one air bag 101, a first intermediate layer 112 composed of a two-layer air bag 101 integrally combined with the first outer layer 111 by heat welding, a second intermediate layer 113 composed of a two-layer air bag 101 integrally combined with the first intermediate layer 112 by heat welding, and a second outer layer 114 composed of one air bag 101 integrally combined with the second intermediate layer 112 by heat welding.

The air bags 101 have a bag-shaped structure. The present invention will be described using the air bags because the blood pressure measurement device 1 is configured to use air supplied by the pump 14. When a fluid other than air is used, the bag-shaped structure may be a fluid bag inflated by the fluid. The air bags 101 are stacked and fluidly communicate in their stacking direction.

The air bags 101 are formed in a rectangular bag shape elongated in one direction. The width of each of the air bags 101 in its widthwise direction is set to the same as the width of the curler 5 in its widthwise direction. The air bags 101 are each formed, for example, by combining two sheet members 106 and welding them at a welding portion 101a by heat in a rectangular frame shape elongated in one direction, as shown in FIGS. 18, 19, 21 and 22. The six-layer air bags 101 are fluidly continuous through openings provided in the sheet members 106 opposed to each other.

In the six-layer air bag 101, the first outer layer 111 and first intermediate layer 112, the first intermediate layer 112 and second intermediate layer 113, and the second intermediate layer 113 and second outer layer 114 bridge-weld their respectively opposed sheet members 106 in a four-sided frame shape smaller than the welding portion 81a positioned on the outer peripheral edge. The bridge welding portion 101b surrounds a plurality of openings to form adjacent air bags 101 integrally with each other and then make them continuous fluidly inside the welding portion 101b.

The first outer layer 111 is formed of one air bag 101 placed on the wrist 200 side. The first outer layer 111 constitutes a first-layer air bag 101 from the wrist 200 side among the six-layer air bags 101.

The first intermediate layer 112 is stacked on the first outer layer 111. The first intermediate layer 112 is formed of a two-layer air bag 101. The first intermediate layer 112 constitutes second-layer and third-layer air bags 101 from the wrist 200 side among the six-layer air bag 101. The first intermediate layer 112 is formed by integrally welding air bags 101 of two layers at the outer peripheral edge. In other words, the first intermediate layer 112 is formed by integrally welding four sheet members 106 in the shape of the outer peripheral edge of the air bag 101.

The second intermediate layer 113 is stacked on the first intermediate layer 112. The second intermediate layer 113 is formed of a two-layer air bag 101. The second intermediate layer 113 constitutes fourth-layer and fifth-layer air bags 101 from the wrist 200 side among the six-layer air bag 101. The second intermediate layer 113 is formed by integrally welding air bags 101 of two layers at the outer peripheral edge. In other words, the second intermediate layer 113 is formed by integrally welding four sheet members 106 in the shape of the outer peripheral edge of the air bag 101.

The second outer layer 114 is formed of one air bag 101 placed on the curler 5 side. The second outer layer 114 constitutes a sixth-layer air bag 101 of the six-layer air bag 101 from the wrist 200 side.

One or more to-be-bonded portions 102 are provided on at least part of an edge portion of the air bags 101 placed adjacently to the curler 5. The to-be-bonded portions 102 are formed of part of the sheet members 86 that constitute the air bags 101.

The present embodiment is directed to a case where two to-be-bonded portions 102 are provided in the longitudinal direction of the air bag 101 at each of the edge portions of the air bag 101 which are located in its widthwise directions. Note that for example, the to-be-bonded portions 102 are provided in the air bag 101 avoiding a position facing the cover portion 5a of the curler 5. In addition, for example, the to-be-bonded portions 102 have a clearance portion 102a for exposing a power supply terminal 8b to the outside at a portion facing the power supply terminal 8b of the power supply portion 8 provided in the curler 5 to be described later. The clearance portion 102a is, for example, an opening capable of exposing the power supply terminal 8b to the outside, and is circular as an example.

The to-be-bonded portions 102 are bonded at least to the outer surface of the curler 5 when the pulling cuff 74 is placed on the inner surface of the curler 5. The to-be-bonded portions 102 placed at the same position in the widthwise direction of the air bags 101 are stacked and welded.

Note that the two to-be-bonded portions 102 are set to have different lengths, for example, in the widthwise direction of the air bags 102. In this example, the two to-be-bonded portions 102 are stacked and welded at one end of the curler 5 in the widthwise direction. Note that the length of the two to-be-bonded portions 102 can appropriately be set and they may be stacked or not if their distal ends can be disposed on the outer surface of the curler 5. When the length is set such that the to-be-bonded portions can be stacked, the distal ends are preferably not extended outward beyond the outer edge of the outer surface of the curler 5.

The connecting portion 103 is, for example, a nipple. The connection portion 103 is provided on the longitudinal-direction center side of the air bags 101 disposed adjacent to the curler 5 and at a position opposed to the third hole portion 5/3 of the cover portion 5a. The distal end of the connecting portion 103 is exposed from one of the two sheet members 106 of the air bags 101, which is opposed to the curler 5. The connecting portion 103 is inserted into the third hole portion 5/3 of the cover 5 and connected to the flow path unit 15.

The notch 104 is provided at a position opposed to the clearance portion 5b provided in the curler 5. The notch 104 is provided in the sixth-layer air bag 101 that forms the second outer layer 114.

As a specific example, as shown in FIGS. 18 and 19, the pulling cuff 74 includes, from the wrist 200 side, a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k and an eighteenth sheet member 106l. Note that the pulling cuff 74 is formed integrally by bonding adjacent sheet members 106 by heat welding.

The seventh sheet member 106a to the eighteenth sheet members 106l are formed in a rectangular shape similar to that of the air bags 101. The seventh and eighth sheet members 106*a* and 106*b* are welded by heat along the peripheral edge shapes of the four sides of the air bag 101 to form an air bag 101 that is a first layer from the wrist 200 side. That is, the seventh and eighth sheet members 106*a* and 106*b* constitute the first outer layer 111.

The eighth and ninth sheet members 106*b* and 106*c* are arranged to face each other and each have a plurality of openings 106*b*1 and 106*c*1 through which two air bags 101 are fluidly connected to each other. The eighth and ninth sheet members 106*b* and 106*c* are bonded integrally by bridging and welding the peripheries of the openings 106*b*1 and 106*bc* by heat in a four-sided frame shape smaller than four sides to which the air bags 101 are welded.

The ninth and tenth sheet members 106*c* and 106*d* are welded by heat along the peripheral edge shape of the four sides of the air bags 101 to form an air bag 101 that is a second layer from the wrist 200 side.

As shown in FIGS. 18 and 19, the tenth and eleventh sheet members 106*d* and 106*e* are arranged to face each other and each have a plurality of openings 106*d*1 and 106*e*1 through which two air bags 101 are fluidly connected to each other. The eleventh and twelfth sheet members 106*e* and 106*f* are welded by heat along the peripheral edge shape of the four sides of the air bags 101 to form an air bag 101 of the third layer from the wrist 200 side.

Note that the ninth, tenth, eleventh and twelfth sheet members 106*e*, 106*d*, 106*e* and 106*f* are integrally welded by heat along the peripheral edge shape of the four sides of the air bags 101 to form a first intermediate layer 112 in which the air bags 101 of the second and third layers are integrally formed.

As shown in FIGS. 18 and 19, the twelfth and thirteenth sheet members 106*f* and 106*g* are arranged to face each other and each have a plurality of openings 106*f*1 and 106*g*1 through which two air bags 101 are fluidly connected to each other. In addition, the twelfth and thirteenth sheet members 106*f* and 106*g* are bonded integrally by bridging and welding the peripheries of the openings 106*f*1 and 106*g*1 by heat in a four-sided frame shape smaller than the four sides to which the air bags 101 are welded.

The thirteenth and fourteenth sheet members 106*g* and 106*h* are welded by heat along the peripheral edge shape of the four sides of the air bags 101 to form an air bag 101 of the fourth layer from the wrist 200 side.

As shown in FIGS. 18 and 19, the fourteenth and fifteenth sheet members 106*h* and 106*i* are arranged to face each other and each have a plurality of openings 106*h*1 and 106*i*1 through which two air bags 101 are fluidly connected to each other. The fifteenth and sixteenth sheet members 106*i* and 106*j* are welded by heat along the peripheral edge shape of the four sides of the air bags 101 to form an air bag 101 of the fifth layer from the wrist 200 side.

Note that the thirteenth sheet member 106*e*, fourteenth sheet member 106*d*, fifteenth sheet member 106*e* and sixteenth sheet member 106*f* are integrally welded by heat along the peripheral edge shape of the four sides of the air bags 101 to form a second intermediate layer 113 in which the air bags 101 of the fourth and fifth layers are integrally formed.

As shown in FIGS. 18 and 19, the sixteenth and seventeenth sheet members 106*j* and 106*k* are arranged to face each other and each have a plurality of openings 106*j*1 and 106*k*1 through which two air bags 101 are fluidly connected to each other. The seventeenth sheet member 106*k* is formed in a shape capable of configuring, for example, the air bags 101 and the to-be-bonded portions 102. The sixteenth and seventeenth sheet members 106*j* and 106*k* are formed integrally with each other by bridging and welding the peripheries of the openings 106*l*1 and 106*k*1 by heat into a four-sided frame shape that is smaller than the four sides to which the air bags 101 are welded.

The seventeenth and eighteenth sheet members 106*k* and 106*l* are welded by heat along the peripheral edge of the four sides of the air bag 101 and cut in a predetermined shape to form the to-be-bonded portion 102 and the air bag 101 having a clearance portion 104 of the sixth layer from the wrist 200 side.

In addition, the eighteenth sheet member 106*l* has, for example, a hole portion 106*b*l1 into which the distal end of the connecting portion 103 can be inserted. In the eighteenth sheet member 106*l*, the connecting portion 103 is placed in the hole portion 106*b*l1, and the periphery of the hole portion 106*b*l1 is welded to the connecting portion 103 by heat. The eighteenth sheet member 106*b*1 is bonded to the inner surface of the curler 5 through the bonding layer 75, and the to-be-bonded portion 102 of the seventeenth sheet member 106*k* is bonded to the outer surface of the curler 5 through the bonding layer 75.

The sheet members 86, 96 and 106 to form the pressing cuff 71, sensing cuff 73 and pulling cuff 74 are formed of thermoplastic resin material. The thermoplastic resin material a thermoplastic elastomer. Examples of the thermoplastic resin material to form the sheet members 86, 96 and 106 may include thermoplastic polyurethane resin (Thermoplastic PolyUrethane, hereinafter referred to as TPU), vinyl chloride resin (Polyvinyl Chloride), ethylene vinyl acetate resin (Ethylene-Vinyl Acetate), thermoplastic polystyrene resin (Thermoplastic PolyStyrene), thermoplastic polyolefin resin (Thermoplastic PolyOlefin), thermoplastic polyester resin (Thermoplastic Polyester), and thermoplastic polyamide resin (Thermoplastic PolyAmide). In the pressing cuff 71 and the sensing cuff 73, among a plurality of sheet members 86 and 106 to form at least the air bags 81 and 101, at least the sheet members 86 and 106 welded to the curler 5 are formed of the same type of material as the curler 5.

For example, The sheet members 86, 96 and 106 are formed using a molding method such as T-die extrusion molding and injection molding. When the sheet members 86, 96 and 106 are formed by the molding methods, they are sized to a predetermined shape, and the sized pieces are bonded by welding or the like to form bag-shaped structures 81, 91 and 101. As the welding method, a high frequency welder and laser welding are used.

The fluid circuit 7 is configured by the case 11, pump 14, flow path unit 15, on-off valves 16, pressure sensors 17, pressing cuff 71, sensing cuff 73 and pulling cuff 74. A specific example of the fluid circuit 7 will be described below.

As shown in FIG. 5, the fluid circuit 7 includes, for example, a first flow path 7*a* that connects the pump 14 to the sensing cuff 73, first pressure sensor 17A and second pressure sensor 17B via the first on-off valve 16A, a second flow path 7*b* that branches from the first flow path 7*a* between the pump 14 and the first on-off valve 16A and connects the pump 14 to the air via the second on-off valve 16B, third on-off valve 16*c* and fourth on-off valve 16D in sequence, a third flow path 7*c* that branches from an intermediate portion of the second flow path 7*b* between the second and third on-off valves 16B and 16C and connects the pump 14 to the pulling cuff 74, and a fourth flow path 7*d* that branches from an intermediate portion of the second flow path 7*b* between the third and fourth on-off valves 16C and 16D and connects the pump 14 to the pressing cuff 71.

In the fluid circuit 7 described above, when the second and third on-off valves 16B and 16C are opened and the first and fourth on-off valves 16A and 16D are closed, the third and fourth flow paths 7c and 7d which branch from the second flow path 7b are connected to the pump 14, and the pump 14 is fluidly connected to the pressing cuff 71 and the pulling cuff.

In the fluid circuit 7, when the first, second and third on-off valves 16A, 16B and 16C are opened and the fourth on-off valve 16D is closed, the third and fourth flow paths 7c and 7d that branch from the first and second flow paths 7a and 7b are connected to the pump 14, and the pump 14 is fluidly connected to the pressing cuff 71, the pulling cuff, and the sensing cuff 73. In the fluid circuit 7, when the second, third and fourth on-off valves 16B, 16C and 16D are opened and the first on-off valve 16A is closed, the second, third and fourth flow paths 7b, 7c and 7d are connected to the pump 14, and the pump 14 is fluidly connected to the pressing cuff 71, pulling cuff 74 and the air. In the fluid circuit 7, furthermore, when the first, second, third and fourth on-off valves 16A, 16B, 16C and 16D are opened, the first, second, third and fourth flow paths 7a, 7b, 7c and 7d are connected to the pump 14, and the pump 14 is fluidly connected to the pressing cuff 71, sensing cuff 73, pulling cuff 74 and the air.

As shown in FIGS. 3, 6 and 15, the power feeding unit 8 is provided in the recess 5c formed in the outer surface at one end of the curler 5 protruding from the device body 3. For example, the power feeding unit 8 is configured to be connectable to a connector provided on a charging cable of a charger.

As shown in FIGS. 2, 6 and 15, the power feeding unit 8 includes a wiring portion 8a, a power feeding terminal 8b and a cover 8c placed in the recess 5c of the curler 5 to cover the wiring portion 8a. One end of the wiring portion 8a is connected to the power feeding terminal 8b, and the other end thereof is connected to the control unit 55. The power feeding terminal 8b is configured by, for example, two circular terminals. For example, the wiring portion 8a and the power feeding terminal 8b are formed of, for example, flexible printed circuits (FPC) in which a conductive metal film or the like is provided on a base film such as polyimide. The cover 8c is formed in the same shape as the recess 5c to cover the recess 5c. When the cover 8c covers the recess 5c, its top surface becomes flush with the widthwise outer surface of the curler 5.

Next, an example of how a blood pressure value is measured by the blood pressure measurement device 1 will be described with reference to FIGS. 27 to 31. FIG. 27 is a flowchart showing an example of blood pressure measurement using the blood pressure measurement device 1, and illustrates both the movement of a user and the operation of the control unit 55. FIGS. 28 to 30 show an example in which the user wears the blood pressure measurement device 1 on the wrist 200.

First, the user attaches the blood pressure measurement device 1 to the wrist 200 (step ST1). Specifically, for example, the user inserts one of the wrists 200 into the curler 5, as shown in FIG. 28.

At the time, in the blood pressure measurement device 1, the device body 3 and the sensing cuff 73 are at opposing positions of the curler 5, so that the sensing cuff 73 is placed in the region where the palm side artery 210 of the wrist 200 exists. As a result, the device body 3 and the pulling cuff 74 are arranged on the back side of the wrist 200. Next, as shown in FIG. 29, the user passes the second strap 62 through the frame-shaped body 61e of the buckle 61b of the first strap 61, using the hand different from the hand on which the blood pressure measurement device 1 is worn. Then, the user pulls the second strap 62 to bring the member on the inner surface side of the curler 5, that is, the cuff structure 6, into close contact with the wrist 200, and inserts the stick 61f in a small hole 62a. Thus, as shown in FIG. 30, the first strap 61 and the second strap 62 are connected, and the blood pressure measurement device 1 is attached to the wrist 200.

Next, the user operates the operation unit 13 to input a command corresponding to the start of blood pressure measurement. In response to the command input operation, the operation unit 13 outputs an electrical signal corresponding to the start of measurement to the control unit 55 (step ST2). Upon receipt of the electrical signal, the control unit 55 opens, for example, the first, second and third on-off valves 16A, 16B and 16C and closes the fourth on-off valve 16D, and drives the pump 14 to supply compressed air to the pressing cuff 71, sensing cuff 73 and pulling cuff 74 via the first, second, third and fourth flow paths 7a, 7b, 7c and 7d (step ST3). Thus, the pressing cuff 71, sensing cuff 73 and pulling cuff 74 start to inflate.

When the pump 14 is driven, it sucks air in the case 11. The inside of the case 11 becomes negative pressure. When the inside of the case 11 becomes negative pressure, air flows into the case 31 from outside the case 11 through the hole 31c.

At this time, water entering the hole 31c from outside the case 11 through the second opening end 31e with air flowing into the hole 31c and reaching the filter 37 is prevented from entering the case 11 by the filter 37. The water here includes user's sweat, rainwater, living water and the like.

The hole 31c has a shape inclined with respect to the center line of the outer case 31. Thus, for example, when the user confirms the display unit 12, if the wrist 200 is moved below the head of the user and the case 11 is positioned so that the display unit 12 can be viewed by the user, the hole 31c is inclined with respect to the horizontal direction. Therefore, the water intruding into the hole 31c is moved toward the second opening end 31e by the action of gravity.

The first and second pressure sensors 17A and 17B detect the pressures of the pressing cuff 71, sensing cuff 73 and pulling cuff 74 and output electrical signals corresponding to the pressures to the control unit 55 (step ST4). Based on the received electrical signals, the control unit 55 determines whether the pressures in the internal spaces of the pressing cuff 71, sensing cuff 73 and pulling cuff 74 have reached a predetermined pressure for blood pressure measurement (step ST5). For example, if the internal pressures of the pressing cuff 71 and pulling cuff 74 have not reached a predetermined pressure and the internal pressure of the sensing cuff 73 has reached a predetermined pressure, then the control unit 55 closes the first on-off valve 16A and supplies compressed air through the second, third and fourth flow paths 7b, 7c and 7d.

When the internal pressures of the pressing cuff 71, pulling cuff 74 and sensing cuff 73 have reached a predetermined pressure, the control unit 55 stops driving the pump 14 (YES in step ST5). At the time, as indicated by alternate long and two short dash lines in FIG. 4, the pressing cuff 71 and pulling cuff 74 are sufficiently inflated, and the inflated pressing cuff 71 presses the back plate 72. Since, furthermore, the pulling cuff 74 presses the curler 5 in a direction in which it is separated from the wrist 200, the strap 4, curler 5 and device body 3 move in the direction, with the result that the pressing cuff 71, back plate 72 and sensing cuff 73 are pulled toward the wrist 200. In addition, when the strap 4, curler 5 and device body 3 are moved in a direction in which they are separated from the wrist 200 by the inflation of the pulling cuff 74, the strap 4 and the curler 5 are moved toward both sides of the wrist 200, and the belt 4, curler 5 and device body 3 are moved in a state where the strap 4 and curler 5 are in close contact with both sides of the wrist 200. Thus, the strap 4 and the curler 5 which are in close contact with the skin of the wrist 200 pull the skin of both sides of the wrist 200 toward the back side of the hand. If the curler 5 can pull the skin of the wrist 200, it may indirectly contact the skin of the wrist 200 through the sheet members 86 and 106, for example.

Furthermore, the sensing cuff 73 is supplied with a predetermined amount of air so that the internal pressure becomes the pressure required for blood pressure measurement, and is thus inflated. Then, it is pressed against the wrist 200 by the back plate 72 pressed by the pressing cuff 71. For this reason, the sensing cuff 73 presses the artery 210 in the wrist 200 and closes the artery 210 as shown in FIG. 31.

In addition, the control unit 55 controls, for example, the third on-off valve 16C to repeatedly open and close the third on-off valve 16C, or adjusts the opening of the third on-off valve 16C to increase the pressure in the internal space of the pressing cuff 71. In the process of this pressure increase, the control unit 55 obtains measurement results of blood pressure values such as systolic blood pressure and diastolic blood pressure, a heart rate and the like, based on the electrical signals output from the second pressure sensor 17B (step ST6). The control unit 55 outputs an image signal corresponding to the obtained measurement result to the display unit 12, and displays the measurement result on the display unit 12 (step ST7). After the blood pressure measurement, the control unit 55 opens the first, second, third and fourth on-off valves 16A, 16B, 16C and 16D.

Upon receipt of the image signals, the display unit 12 displays the measurement results on the screen. The user confirms the measurement results by looking at the display unit 12. After the measurement, the user removes the stick 61f from the small hole 62a, removes the second strap 62 from the frame-shaped body 61e, and pulls the wrist 200 off the curler 5, thereby detaching the blood pressure measurement device 1 from the wrist 200.

In the blood pressure measurement device 1 according to the present embodiment configured as described above, the on-off valve 16 is disposed in the outer case 31 away from the pump and the power supply unit 18 in the axial direction D of the outer case 31. The blood pressure measurement device 1 can thus be decreased in thickness in the axial direction D of the outer case 31 of the case 11.

The power supply unit 18 is placed on the pump 14, and an edge portion of the surface of the power supply unit 18 facing the pump 14 is fixed to the pump 14 by the double-sided tape 38. For this reason, a gap S corresponding to the thickness of the double-sided tape 38 is provided between the pump 14 and the central side of the surface 18a of the power supply unit 18 facing the pump 14. Therefore, even though the surface of the power supply unit 18 on the pump 14 side is inflated toward the pump 14 when the power supply unit is inflated due to its deterioration or the like, the power supply unit 18 can be prevented from being in direct contact with the pump 14. Heat generated in the pump 14 can thus be prevented from being transmitted to the power supply unit 18.

The first opening end 31d, which is an opening end of the hole 31c in the case 11, is provided to face the gap S in the first direction. Thus, when the pump 14 is driven, air flowing from outside the case 11 into the case 11 through the hole 31c can be caused to flow into the gap S smoothly. The air flowing from outside the case 11 allows the pump 14 to be cooled with efficiency.

The power supply unit 18 is opposed, at one end in the longitudinal direction, to the pump 14 in the axial direction D of the outer case 31. Thus, when the power supply unit 18 is inflated toward the pump 14 due to its deterioration or the like, a gap between the first opening end 31d in the first direction of the power supply unit 18 and the first opening end 31d in the first direction of the pump 14 is increased.

As a result, air easily flows into the gap S between the pump 14 and the power supply unit 18 to improve the cooling efficiency of the pump 14 and the power supply unit 18. The power supply unit 18 can thus be prevented from deteriorating.

The double-sided tape 38 is provided at an edge portion of the power supply unit 18 along the longitudinal direction of the surface 18a opposed to the pump 14. The second and third suction holes 14d2 and 14d3 of the pump 14 are located to face an edge portion of the surface 14c along the longitudinal direction of the power supply unit 18.

Therefore, air from the first opening end 31d of the hole 31c can be caused to flow into the gap S smoothly through between two double-sided tapes 38. In addition, when the central part of the surface 18a of the power supply unit 18 is inflated due to its deterioration or the like, one end of the power supply unit 18 in the longitudinal direction is separated from the pump 14. As a result, a gap between the power supply unit 18 and the pump 14 is increased. Therefore, even though the power supply unit 18 is inflated, the second and third suction holes 14d2 and 14d3 can be prevented from being closed by the power supply unit 18.

The hole 31c is formed in a shape inclined with respect to the center line of the outer case 31. Since, therefore, the flow path of air guided to the pump 14 through the hole 31c and the gap S is not bent largely, the flow path of air including the hole 31c and the gap S can be decreased in resistance.

The second opening end 31e of the hole 31c, which is provided on the outer surface 31f of the outer case 31, is covered by an end portion of the strap 4 on the case 11 side. Since, therefore, the hole 31c is covered with the strap 4, it is prevented from being exposed outside, with the result that the hole 31c can be made inconspicuous and thus the blood pressure measurement device 1 is improved in its designability.

In the blood pressure measurement device 1, the hole 31c is formed into a linear hole inclined with respect to the axial direction D of the outer case 31. Even though water enters the hole 31c from outside the case 11, it is easily moved toward the second opening end 31e.

The blood pressure measurement device 1 has a filter 37 at the first opening end 31d of the hole 31c. Thus, even though water enters the hole 31c, the filter 37 can prevent water from entering the case 11. The blood pressure measurement device 1 can thus be improved in its waterproof property.

As described above, according to the blood pressure measurement device 1 of the present embodiment, the case 11 can be thinned.

In the above-described example, the outer case 31 is formed in a cylindrical shape, but the present invention is not limited to the example. The outer case 31 may be formed, for example, in a rectangularly cylindrical shape.

The above-described embodiment is merely an example of the present invention in all respects. Needless to say, various improvements and modifications can be made without departing from the scope of the present invention. That is, in implementing the present invention, a specific configuration according to the embodiment may be adopted as appropriate.

REFERENCE SIGNS LIST

1 . . . Blood Pressure Measurement Device
3 . . . Device Body
4 . . . Strap
5 . . . Curler
5a . . . Cover Portion
5b . . . Clearance Portion
5d . . . Insert member
6 . . . Cuff Structure
7 . . . Fluid Circuit
7a . . . First Flow Path
7b . . . Second Flow Path
7c . . . Third Flow Path
7d . . . Fourth Flow Path
8 . . . Power Feeding Unit
11 . . . Case
12 . . . Display Unit
13 . . . Operation Unit
14 . . . Pump
14a . . . Side
14b . . . Side
14c . . . Surface
14d . . . Suction Hole
14d1 . . . First Suction Hole
14d2 . . . Second Suction Hole
14d3 . . . Third Suction Hole
15 . . . Flow Path Unit
16 . . . On-Off Valve
16A . . . First On-Off Valve
16B . . . Second On-Off Valve
16C . . . Third On-Off Valve
16D . . . Fourth On-Off Valve
17 . . . Pressure Sensor
17A . . . First Pressure Sensor
17B . . . Second Pressure Sensor
18 . . . Power Supply Unit
19 . . . Vibration Motor
20 . . . Control Board
31 . . . Outer Case
31a . . . Lug
31b . . . Spring Rod
31c . . . Hole
31d . . . first opening end
31e . . . second opening end
31f . . . Outer Surface
31h . . . Chamfered Portion
32 . . . Windshield
33 . . . Base
35 . . . Back Cover
35a . . . First Fastening Member
35b . . . Second Fastening Member
36 . . . Seal Member
37 . . . Filter
38 . . . Double-Sided Tape
39 . . . Support Plate
41 . . . Button
42 . . . Sensor
43 . . . Touch Panel
51 . . . Board
52 . . . Acceleration Sensor
53 . . . Communication Unit
54 . . . Storage Unit
55 . . . Control Unit
56 . . . Main CPU
57 . . . Sub-CPU
61 . . . First Strap
61a . . . Strap Portion
61b . . . Buckle
61c . . . First Hole portion
61d . . . Second Hole portion
61e . . . Frame-Shaped Body
61f . . . Stick
62 . . . Second Strap
62a . . . Small Hole
62b . . . Third Hole Portion
71 . . . Pressing Cuff
72 . . . Back Plate
72a . . . Groove
73 . . . Sensing Cuff
74 . . . Pulling Cuff
81 . . . Air Bag
84 . . . Connecting Portion
86 . . . Sheet Member
86a . . . First Sheet Member
86b . . . Second Sheet Member
86b1 . . . Opening
86c . . . Third Sheet Member
86c1 . . . Opening
86d . . . Fourth Sheet Member
91 . . . Air Bag
92 . . . Flow Path Body
93 . . . Connecting Portion
96 . . . Sheet Member
96a . . . Fifth Sheet Member
96b . . . Sixth Sheet Member
101 . . . Air Bag
103 . . . Connecting Portion
106 . . . Sheet Member
106a . . . Seventh Sheet Member
106b . . . Eighth Sheet Member
106b1 . . . Opening
106c . . . Ninth Sheet Member
106c1 . . . Opening
106d . . . Tenth Sheet Member
106d1 . . . Opening
106e . . . Eleventh Sheet Member
106e1 . . . Opening
106f . . . Twelfth Sheet Member
106f1 . . . Opening
106g . . . Thirteenth Sheet Member
106g1 . . . Opening
106h . . . Fourteenth Sheet Member
106h1 . . . Opening
106i . . . Fifteenth Sheet Member
106i1 . . . Opening
106j . . . Sixteenth Sheet Member
106j1 . . . Opening
106k . . . Seventeenth Sheet Member
106k1 . . . Opening
106l . . . Eighteenth Sheet Member
200 . . . Wrist
210 . . . Artery

What is claimed is:

1. A blood pressure measurement device configured to be attached to a wrist, comprising:
a case including an outer case formed in a cylindrical shape and having two pairs of lugs provided at positions symmetrical in a circumferential direction of an outer surface, and a windshield covering one end of the outer case;

a strap including a first strap provided on one pair of lugs through a spring rod and a second strap provided on the other pair of lugs through a spring rod;

a plurality of valves provided in a flow path that supplies a fluid to a cuff inflated by the fluid in the outer case in a position which is closer to one side of the outer case than a center thereof in a second direction orthogonal to a first direction from the one pair of lugs to the other pair of lugs and orthogonal to an axial direction of the outer case;

a pump provided in the outer case closer to the center of the outer case with respect to the valves in the second direction and on one side from the center of the outer case in the first direction; and a power supply unit cased in the outer case, disposed on the pump alongside the windshield in the axial direction of the outer case and opposed to the pump;

wherein:

the pump and the power supply unit are disposed with a gap therebetween;

the pump is provided with a suction hole on a surface thereof opposite to the power supply unit;

the device comprises a hole portion formed between each of the pairs of lugs of the outer case to pass through the outer case and having an opening end on an inner surface of the outer case, the opening end being located at a position opposed to the gap in the first direction; and the hole portion extends linearly, and one opening end of the hole portion is provided on the outer surface of the outer case closer to the wrist, and another opening end thereof is provided on the inner surface of the outer case closer to the windshield than the one opening end.

2. The blood pressure measurement device of claim 1, further comprising a double-sided tape provided between opposing surfaces of the power supply unit and the pump to fix the power supply unit and the pump at both edge portions of the pump in the second direction.

3. The blood pressure measurement device of claim 1, wherein the power supply unit is formed in a long shape in one direction, a longitudinal direction of the power supply unit is along the first direction, and one side of the power supply unit in the longitudinal direction is opposed to face the pump.

4. The blood pressure measurement device of claim 3, wherein the suction hole is formed at least on a surface of the pump opposed to the power supply unit on a hole portion side in the first direction and at either end of the pump in the second direction.

5. The blood pressure measurement device of claim 1, wherein:

the opening end of the hole portion formed between the one pair of lugs, which is provided on the outer surface of the outer case, is covered with the first strap; and the opening end of the hole portion formed between the other pair of lugs, which is provided on the outer surface of the outer case, is covered with the second strap.

* * * * *